US012582497B2

(12) United States Patent     (10) Patent No.:    US 12,582,497 B2

Wortmann et al.               (45) Date of Patent:     Mar. 24, 2026

(54) HEADREST FOR AN IMMOBILIZATION SYSTEM

(71) Applicant: BRAINLAB AG, Munich (DE)

(72) Inventors: Manuel Wortmann, Munich (DE); Andreas Bereket, Munich (DE)

(73) Assignee: Brainlab SE, Munich (DE)

( * ) Notice: Subject to any disclaimer, the term of this patent is extended or adjusted under 35 U.S.C. 154(b) by 0 days.

(21) Appl. No.: 18/387,141

(22) Filed: Nov. 6, 2023

(65) Prior Publication Data

US 2024/0065798 A1     Feb. 29, 2024

Related U.S. Application Data

(63) Continuation of application No. 16/090,424, filed as application No. PCT/EP2018/058866 on Apr. 6, 2018, now abandoned.

(30) Foreign Application Priority Data

Apr. 20, 2017    (WO) ................. PCT/EP2017/059420

(51) Int. Cl.
     *A61B 90/18*       (2016.01)
     *A61B 6/04*        (2006.01)
           (Continued)

(52) U.S. Cl.
     CPC .............. *A61B 90/18* (2016.02); *A61B 90/14* (2016.02); *A61B 6/0421* (2013.01); *A61B 2090/101* (2016.02); *A61N 2005/1097* (2013.01)

(58) Field of Classification Search
     CPC ......... A61B 90/10; A61B 90/14; A61B 90/18; A61B 2090/101; A61B 6/04;
           (Continued)

(56) References Cited

U.S. PATENT DOCUMENTS

| | | | | | |
|---|---|---|---|---|---|
| 2,581,802 | A | * | 1/1952 | Lyons | .................. A47G 9/1009 |
| | | | | | 5/643 |
| 5,033,138 | A | * | 7/1991 | Hong | ................... A47G 9/1009 |
| | | | | | 5/636 |

(Continued)

FOREIGN PATENT DOCUMENTS

| | | |
|---|---|---|
| DE | 2017159 A1 | 11/1971 |
| WO | 2006084059 A2 | 8/2006 |
| WO | 2014205448 A1 | 12/2014 |

OTHER PUBLICATIONS

Brainlab, "Stereotactic Components: Headrest," Feb. 22, 2018, p. 1.

(Continued)

*Primary Examiner* — Alireza Nia

*Assistant Examiner* — Gina Mccarthy

(74) *Attorney, Agent, or Firm* — Tucker Ellis LLP

(57) ABSTRACT

A headrest for an immobilization system for immobilizing at least a part of a patient is provided. The headrest includes a supporting structure and a sheet-like formed elastic panel attached to the supporting structure on at least two opposite sides of the elastic panel. The elastic panel is configured to support at least a part of a head and/or at least a part of a neck of a patient, wherein at least a part of the elastic panel is stretchable and configured to stretch when said at least part of the head and/or neck of the patient is arranged on the elastic panel, such that a shape of said at least part of the elastic panel is formed corresponding to a shape of said at least part of the head and/or neck of the patient.

21 Claims, 8 Drawing Sheets

(51) Int. Cl.
    *A61B 90/10*        (2016.01)
    *A61B 90/14*        (2016.01)
    *A61N 5/10*        (2006.01)

(58) Field of Classification Search
    CPC ..... A61B 6/0407; A61B 6/0421; A61B 6/501;
          A61N 5/00; A61N 5/10; A61F 5/37;
          A61F 5/3707; A61G 7/07; A61G 7/072;
          A61G 7/1084; A61G 13/121; A61G
          15/12; A61G 15/125
    See application file for complete search history.

(56)           References Cited

U.S. PATENT DOCUMENTS 5,067,483 A * 11/1991 Freed ................... A61H 1/0218
                           602/18
5,702,406 A * 12/1997 Vilsmeier ............. A61B 90/18
                           128/845

2009/0151731 A1   6/2009  Scott
2010/0000549 A1   1/2010  Nieberding
2015/0047652 A1   2/2015  De Mooij
2016/0150837 A1   6/2016  Kaforey et al.
2016/0317243 A1  11/2016  Garcia Coni
2018/0235824 A1   8/2018  Nordgren
2019/0175382 A1   6/2019  Scott

OTHER PUBLICATIONS

"Silverman Head Supports," http://www.qfix.com/qfix-products/intracranial-head-and-neck.asp?CID=2&PLID=48, Feb. 22, 2018, p. 1-3.

"Timo Headrest," CIVO Radiotherapy, https://civcort.com/ro/head-necj/timo-headrests/timo-headrests-HN10.htm, Feb. 22, 2018, pp. 1-2.

* cited by examiner

HEADREST FOR AN IMMOBILIZATION SYSTEM

RELATED APPLICATION DATA

This application is a continuation of U.S. patent application Ser. No. 16/090,424 filed on Oct. 1, 2018, which is a national phase application of International Application No. PCT/EP2018/058866 filed Apr. 6, 2018, which claims priority from International Application No. PCT/EP2017/059420 filed Apr. 20, 2017, which are hereby incorporated herein by reference.

FIELD OF THE INVENTION

Generally, the present invention relates to non-invasive immobilization of at least a part or body part of a patient. Particularly, the present invention relates to a headrest for an immobilization system for immobilizing at least a part or body part of a patient. The present invention further relates to a use of such headrest in an immobilization system, to an immobilization system comprising such headrest, and to a method for immobilizing at least a part of a head and/or neck of a patient. Specifically, the headrest and/or the immobilization system according to the present invention may be used in the context of orthopaedic, therapeutic and/or diagnostic procedures, such as e.g. radiotherapy, radiosurgery, radiation treatment and/or diagnostic imaging.

TECHNICAL BACKGROUND

Immobilization systems are used in the context of orthopaedic, therapeutic and/or diagnostic procedures for immobilizing, positioning and/or fixing at least a part or body part of a patient. In such procedures, usually the part or body part in question is immobilized, positioned and/or fixed relative to a fixed structure in order to ensure a high reproducibility of the body part's spatial position during the procedure.

For instance, to immobilize at least a part of a patient's head, a neck and/or a patient's shoulder for radiation therapy and/or diagnostic imaging, the body part can be connected to a fixed supporting structure or fixture, such as e.g. a patient bed, in a spatially fixed arrangement and therefore in a reproducible position relative to a radiation and/or imaging device. For this purpose, immobilization devices or immobilization systems may be used which provide a rigid connection between the head and the fixture, wherein the head can be held within a headrest supporting the rear head or the fore head and for example a mask that comprises at least one layer of a low temperature thermoplastic material, which previously has been individually adapted to the head in a heated condition thereof so that, after the mask has cooled down and cured, the mask tightly fits to the head to be immobilized.

Generally, the headrest of an immobilization system can be configured to support the patient's head and to place it in a position that is appropriate for a specific procedure, such as e.g. a radiotherapy treatment with a specific treatment indication.

A drawback of conventional headrests may be that they are made of dimensionally relatively stable, non-elastic material, such as e.g. relatively rigid foam, hard plastic or composite material. Therefore, such headrests usually offer only one pre-shaped contour for the rear head or the fore head with no or only limited individual adaption to the anatomy of the patient. Moreover, a tight fit of such headrests to the patient's anatomy can only be achieved by additional means, such as an extra vacuum cushion arranged between the headrest and the patient's head. As the anatomy of different patients may strongly vary, usually multiple headrests offering different contours for different anatomies or heads should be available.

Apart from that, at least some of the materials used in conventional headrests, especially those made of plastic or composite material, may not be comfortable for the patient and may be slippery, e.g. in case their surface is smooth.

A further drawback of conventional headrests may be that a significant amount of radiation is absorbed by the material constituting the headrests during the radiation therapy, radiotherapy, radiation treatment, radiosurgery and/or diagnostic imaging.

It is, therefore, desirable to provide for an improved headrest for an immobilization system and an improved immobilization system, in which some of or all of the above-mentioned drawbacks are resolved or overcome.

Particularly, the headrest according to the present invention can be used for supporting at least a part of a patient's head, neck and/or shoulders for non-invasive patient immobilization and reproducible positioning, e.g. during radiosurgery, stereotactic radiosurgery, radiotherapy, radiation treatment, and/or diagnostic imaging, for instance in connection with a cranial mask system, such as the ExecTrac® Frameless SRS System of Brainlab AG.

Aspects of the present invention, examples and exemplary features or steps and their embodiments are disclosed in the following. Different aspects, embodiments, examples and exemplary features of the invention can be combined in accordance with the invention wherever technically expedient and feasible.

EXEMPLARY SHORT DESCRIPTION OF THE INVENTION

In the following, a short description of some of the features of the present invention is given which shall not be understood to limit the invention only to the features or a combination of the features described in this section.

According to the present disclosure, a headrest for an immobilization system for immobilizing at least a part or body part of a patient is provided. The headrest and/or the immobilization system may particularly be configured for immobilizing at least a part of a head, at least a part of neck, and/or at least a part of a shoulder of the patient. Therein, the term immobilizing may refer to positioning and/or fixing the at least part of the patient, for instance relative to a fixed support structure or fixture, such as e.g. a patient bed, on which the patient may be arranged during therapeutic and/or diagnostic procedures, such as e.g. radiotherapy, radiosurgery, radiation treatment and/or diagnostic imaging.

The headrest comprises a supporting structure and a sheet-like formed elastic panel attached laterally to the supporting structure on at least two opposite and/or opposing sides of the elastic panel. The elastic panel is configured to support at least a part of the head, at least a part of the neck and/or at least a part of the shoulders of the patient. Therein, at least a part of the elastic panel is stretchable and configured to stretch when said at least part of the head, neck and/or shoulders of the patient is arranged on the elastic panel, such that a shape of said at least part of the elastic panel is formed corresponding to a shape of said at least part of the head, neck and/or shoulders of the patient.

According to an example of the invention, the at least part of the elastic panel is reversibly deformable and/or reversibly stretchable at room temperature, such as e.g. at a temperature between 15° C. and 35° C., preferably between 18° C. and 30° C. It is emphasized, however, that the elastic panel and/or a material thereof may also be elastic, reversibly deformable and/or reversibly stretchable at a temperature other than the above-mentioned temperature ranges. Moreover, it is emphasized that the elastic panel and/or a material thereof may have different physical and/or deformation properties, such as e.g. non-elastic, viscoelastic and/or thermoplastic deformation properties, at a temperature other than the above-mentioned temperature ranges. By way of example, the elastic panel may be elastic, reversibly deformable and/or reversibly stretchable at room temperature and thermoplastic at a temperature above room temperature, such as e.g. above 35° C., preferably above 30° C.

Generally, the term elastic describes an ability of the elastic panel and/or a material thereof to resume its normal shape after being deformed, stretched and/or compressed. Moreover, the elasticity of the elastic panel may be defined as the ability of the elastic panel and/or a material thereof to resist a distorting and/or deforming influence, such as e.g. a force exerted by the patient's head, neck and/or shoulders, to the elastic panel, and to return partly or entirely to its original size, form and/or shape when that influence or force is removed.

Generally, the elastic panel of the headrest, its constituents, components and/or the material of the headrest may allow a deformation, a stretch and/or an elongation in one or more spatial directions of more than about 1%, for instance more than about 5%, preferably more than about 10%, more preferably more than about 30%, and even more preferably more than about 50% relative to a size and/or elongation, in which no force is exerted. Moreover, the deformation, stretch and/or elongation may be in a range of about 1% to about 20%, for example about 1% to about 15%, preferably about 3% to about 14%, more preferably about 3% to about 10%, and even more preferably about 4% to about 9%, relative to the size and/or elongation, in which no force is exerted. When the force stretching the elastic panel is removed, the elastic panel may resume its original size, elongation, form and/or shape. Therein, the original size, elongation, form and/or shape may refer to a state of the elastic panel, in which no external force is exerted on the elastic panel (also referred to as rest position of the headrest hereinafter). Further, the elastic panel may resume its original size, elongation, form and/or shape autonomously due to its elastic properties. In other words, no external force may be required to bring the elastic panel partly or entirely back into its original size, elongation, form and/or shape after removal of the force that stretched the elastic panel.

The headrest according to the present invention with its elastic panel advantageously adapts, particularly automatically, to an anatomy of the patient, such as an anatomy of the at least part of the head, neck and/or shoulders. Accordingly, the elastic panel or at least a part thereof may form precisely and tightly to a surface of the patient that rests on and/or is in contact with the headrest and/or the elastic panel.

Moreover, the headrest advantageously allows to freely and/or steplessly position the patient's head, e.g. to best fit a certain treatment indication. By way of example, a chin of the patient can be positioned in an upwards or downwards tilted position. Also, a lateral tilting of the patient's head is possible.

Apart from that, due to a reduced design of the entire headrest, particularly the elastic panel, compared to conventional headrests that are currently used, significantly less radiation may be absorbed in the headrest, particularly in an anterior-posterior direction. Further, a comfort for the patient may be significantly improved with respect to conventional headrests.

GENERAL DESCRIPTION OF THE INVENTION

In this section, a description of the general features of the present invention is given for example by referring to possible or exemplary embodiments of the invention.

As stated above, it may be desirable to provide for an improved headrest for an immobilization system and an improved immobilization system, in which some of or all of the above-mentioned drawbacks of currently used headrests are resolved or overcome.

This is achieved by the subject-matter of the independent claims, wherein further embodiments are incorporated in the dependent claims and the following description.

According to a first aspect of the invention, there is provided a headrest for an immobilization system for immobilizing at least a part of a patient. The headrest comprises a supporting structure and a sheet-like formed elastic panel attached and/or fixed to the supporting structure on at least two opposite and/or opposing sides of the elastic panel. The elastic panel is configured to support and/or carry at least a part of a head and/or at least a part of a neck of a patient. Therein, at least a part of or the entire elastic panel is stretchable and configured to stretch when said at least part of the head and/or neck of the patient is arranged, situated and/or located on the elastic panel, such that a shape and/or form of said at least part of the elastic panel is formed corresponding to a shape of said at least part of the head and/or neck of the patient.

Generally, the headrest may refer to a head support for supporting the at least part of the patient's head and/or neck. It is emphasized, however, that the headrest according to the present invention is not limited to supporting and/or immobilizing the at least part of the head and/or neck. In contrast, the headrest may also be configured or used to immobilize other parts or body parts of the patient. Specifically, by means of the headrest at least a part of a shoulder, shoulders, and/or a part of a spine of the patient may be immobilized, positioned and/or fixed. For reasons of simplicity, however, it is primarily referred to an immobilization of the patient's head and/or neck (or parts thereof) in the following, without any limitation of the present invention.

The headrest according to the present invention with its elastic panel advantageously adapts, particularly automatically adapts, to a shape, form and/or anatomy of the at least part of the patient's head and/or neck. Accordingly, the elastic panel or the at least part thereof may form, e.g. precisely and/or tightly, to a surface of the at least part of the patient that rests on and/or is in contact with the headrest and/or the at least part of the elastic panel. In other words, when the patient places its head and/or neck on the headrest, the elastic panel may surround, abut and/or enclose the at least part of the patient's head and/or neck. This advantageously allows to immobilize the at least part of the patient's head and/or neck in an effective and reliable manner. Further, by being formed according to and/or in correspondence with the shape or anatomy of the head and/or neck, a comfort for the patient may significantly be increased or improved. Moreover, due the elastic properties of the elastic panel and/or its stretchability, the headrest may be used for any patient, e.g. irrespective of a size and/or a weight of the patient's head and/or neck. Accordingly, the headrest may be used for patients of any age or any anatomy.

The term "immobilization" of the patient's head and/or neck in the context of the present disclosure may mean that the patient's head and/or neck (or parts thereof) is positioned and/or fixed, e.g. relative to a fixed supporting structure or fixture, such as a patient bed, on which the patient may be arranged. Accordingly, by means of the headrest, the patient's head and/or neck may be positioned and/or fixed in a spatially fixed arrangement and/or in a reproducible position, e.g. relative to a radiation or imaging device. Likewise, the term immobilization system may refer to a system, device, arrangement or apparatus configured to immobilize, position and/or fix at least a part or body part of the patient, particularly at least a part of the patient's head and/or neck.

The supporting structure may refer to a fixture or a supporting element. Preferably, the supporting structure or at least a part thereof may be dimensionally stable, rigid and/or solid. However, the supporting structure or a part thereof may also be elastic and/or flexible, wherein an elasticity or flexibility of the supporting structure may be smaller or less than an elasticity of the elastic panel. The supporting structure may be configured to hold the elastic panel in place, particularly in a rest position of the headrest or the elastic panel, in which no external force (at least no force other than the gravitational force acting on the headrest itself) is exerted on the headrest and/or the elastic panel. The elastic panel may be laterally attached and/or fixed to the supporting structure, wherein the two opposite or opposing sides of the elastic panel may be fixed, mechanically fixed, attached and/or coupled to the supporting structure, e.g. by means of a bolt connection, a glue connection, a clamp connection or any other suitable connection. The elastic panel may also be detachably attached to the supporting structure. Moreover, the supporting structure may be configured to at least partly pre-stress and/or pretension the elastic panel in the rest position. Apart from that, the supporting structure may be configured to connect to another part of an immobilization system, such as e.g. a base of a thermoplastic mask that may be placed on the patient's face or head to further immobilize, position and/or fix the patient's head and/or neck.

The term sheet-like formed elastic panel may, in the context of the present disclosure, refer to a sheet-like, foil-like and/or membrane-like shaped panel or element having elastic properties. Accordingly, the elastic panel and/or at least a part thereof may be reversibly deformable, such that the elastic panel stretches, reversibly stretches, reversibly elongates and/or reversibly deforms under or in response to a force exerted by the patient's head and/or neck. Further, the elastic panel may return partly or entirely to its original size, form and/or shape, e.g. to its rest position, when that force is removed. The sheet-like form of the elastic panel may mean that a length and/or width of the elastic panel may be larger, particularly, significantly larger, than a thickness of the elastic panel. Therein, the width of the elastic panel may be measured along a transverse axis of the elastic panel or the headrest, e.g. between the two opposite sides of the elastic panel that are attached to the supporting structure. Further, the length of the elastic panel may be measured along a longitudinal axis of the headrest or the elastic panel, wherein this longitudinal axis may be substantially parallel to the two opposite sides of the elastic panel attached to the supporting structure. Accordingly, the thickness of the sheet-like elastic panel may be measured transverse (or perpendicular) to both the transverse axis and the longitudinal axis. By way of example, the thickness of the elastic panel may be less than about 10%, particularly less than about 5%, preferably less than about 3%, and even more preferably less than about 1% of the width and/or length of the elastic panel. For instance, the thickness of the elastic panel may range from about 0.1 mm to 5 cm, e.g. from about 0.1 mm to about 2 cm, preferably from about 0.2 mm to about 0.5 cm, and more preferably from about 0.3 mm to about 3 mm.

Moreover, the term "stretching of the sheet-like elastic panel" may mean that the elastic panel elongates under the force exerted by the patient's head and/or neck. Therein, the length and/or the width of the elastic panel may be increased and/or elongated with respect to the rest position by at least 1%, e.g. by at least 5%, preferably by at least 10%, more preferably by at least 30%, and even more preferably by at least 50%. Moreover, the length and/or width of the elastic panel may be increased and/or elongated with respect to the rest position by about 1% to about 20%, for example about 1% to about 15%, preferably about 3% to about 14%, more preferably about 3% to about 10%, and even more preferably about 4% to about 9%. Similarly, the thickness of the sheet-like elastic panel may be reduced and/or decreased with respect to the rest position by at least 1%, e.g. by at least 5%, preferably by at least 10%, more preferably by at least 30%, and even more preferably by at least 50%. Accordingly, the thickness of the elastic panel may be reduced and/or decreased with respect to the rest position in a range of about 1% to about 20%, for example about 1% to about 15%, preferably about 3% to about 14%, more preferably about 3% to about 10%, and even more preferably about 4% to about 9%.

An elasticity, a stretchability, a stretch, elongation, increase in length and/or increase in width of the elastic panel may be determined as exemplary described in the following. A line may be drawn on the elastic panel in the rest position (i.e. without exertion of an external force onto the elastic panel) and a length of the line may be determined or measured in the rest position. Subsequently, an external force, preferably a constant force, may be exerted on the elastic panel or a part thereof, thereby stretching at least a part of the elastic panel. The length of the line may then be determined or measured when the external force is exerted, e.g. in a stretched state of the elastic panel. The elasticity, stretchability, stretch, elongation, increase in length and/or increase in width may then be determined based on a ratio of the length of the line in the rest position and the length of the line when the external force is exerted. Preferably, the line is drawn along the shortest path between two opposing edges of the elastic sheet through the point where the elastic sheet is deformed the most from its original state, e.g. where the maximum force is exerted. The force is preferably exerted by a typical patients head and/or neck and/or shoulders and/or a phantom simulating a typical patients head and/or neck and/or shoulders. Preferably, the stretch is determined for a multitude of lines along a path between any two opposing edges and the stretch of the elastic panel is for example defined as the maximum value determined from any of the lines.

Rephrasing the first aspect of the invention, the headrest comprises the supporting structure, e.g. a rigid frame structure or fixture, and the sheet-like elastic panel, wherein the sheet-like elastic panel may refer to a flexible, stretchable and/or elastic portion or part of the headrest. The patient's head and/or neck may be arranged on and/or rest on the elastic panel. When the head and/or neck is placed on the elastic panel, it stretches and/or elongates in response to the force exerted thereon, for instance until its stretching limit is reached for that force. This way, the elastic panel, a part thereof, a surface thereof and/or a material thereof encloses, particularly tightly encloses, at least a part of the head and/or neck, which is placed on it, regardless of its size and/or shape. This may allow to efficiently and reliably immobilize, position and/or fix the patient's head and/or neck, while also significantly increasing or improving a comfort for the patient compared to conventional headrests currently used. Moreover, this allows the headrest to be re-used for any patient, regardless of an anatomy of the patient, such as e.g. the size of the head and/or neck. In other words, the headrest and/or the elastic panel can advantageously be reversibly adapted to arbitrary sizes, shapes and/or anatomies of the heads and/or necks of different patients.

Moreover, by means of the headrest the head can advantageously be moved freely and/or stepless into any desired position. In other words, the headrest with its elastic panel advantageously allows to freely and/or steplessly position the patient's head, e.g. to best fit a certain treatment indication. By way of example, a chin of the patient can be positioned in an upwards or downwards tilted position. Also, a lateral tilting of the patient's head is possible. Generally, the elastic panel and/or the material thereof can be designed or configured in such a way that the head and/or neck can be positioned in an approximately horizontal positon, e.g. a lying position of the patient.

Apart from that, due to the sheet-like form of the elastic panel having a thickness that is significantly smaller than the width and/or the length thereof, significantly less radiation may be absorbed in the headrest and/or the elastic panel compared to currently used conventional headrests, particularly in an anterior-posterior direction. However, also with a beam having an impinging direction tilted with respect to the anterior-posterior direction, e.g. tilted by about 90°, significantly less radiation may be absorbed in the headrest and/or elastic panel compared to currently used conventional headrests.

According to an embodiment of the present invention, the at least part of the elastic panel is reversibly deformable and/or reversibly stretchable at room temperature. In the context of the present disclosure, the room temperature may range from about 15° C. to about 35° C., preferably from about 18° C. to about 30° C. By means of the reversible deformability and/or the reversible stretchability of the elastic panel at room temperature, it may be ensured that the elastic panel or at least a part thereof encloses the part of the patient's head and/or neck during the treatment or procedure, in which the headrest may be used, thereby immobilizing the head and/or neck in an effective manner, particularly without any additional heat source or the like. Accordingly, the reversible stretchability and/or deformability of the elastic panel at room temperature may mean that the elastic panel exhibits substantially the same elastic and/or deformation properties over the room temperature ranges specified above. In other words, at least in the temperature ranges specified above the elastic and/or deformation properties of the elastic panel may be substantially constant and/or substantially temperature-independent.

According to an embodiment of the present invention, the elastic panel comprises one or more elastic sheets for supporting said at least part of the head and/or neck of the patient. The elastic sheets may be membrane-like and/or foil-like formed, wherein each of the elastic sheets may have a thickness that is smaller, particularly significantly smaller, than a length and/or a width of the respective elastic sheet. Therein, the length of the elastic panel may define or substantially equal the length of the at least one elastic sheet. Likewise, the width of the elastic panel may define or substantially equal the width of the at least one elastic sheet. By way of example, the thickness of the at least one elastic sheet may be less than about 10%, particularly less than about 5%, preferably less than about 3%, and even more preferably less than about 1% of the width and/or length of the at least one elastic sheet. For instance, the thickness of the at least one elastic sheet may range from about 0.1 mm to 5 cm, e.g. from about 0.1 mm to about 2 cm, preferably from about 0.2 mm to about 0.5 cm, and more preferably from about 0.3 mm to about 3 mm.

Accordingly, the elastic panel may refer to an arrangement of one or more elastic sheets. Therein, each of the elastic sheets may be attached to the supporting structure on two opposite sides of the respective elastic sheet. If the elastic panel comprises a plurality of elastic sheets, the elastic sheets may be arranged substantially parallel to each other.

According to an embodiment of the present invention, the elastic panel comprises at least one material selected from the group consisting of polymer-based elastic material, silicone material, rubber material, and elastic foam. Further, the material of the elastic panel may be biocompatible and/or cleaning-resistant.

According to an embodiment of the present invention, the elastic panel comprises a middle region and at least one reinforced region, wherein the middle region is more stretchable than the at least one reinforced region. The middle region may refer to a middle head support portion of the elastic panel and/or may be configured to support a middle head having substantially the largest circumference with respect to other portions of the head. Further, the at least one reinforced region may refer to a neck support portion of the elastic panel configured to support at least a part of the neck. Alternatively, the at least one reinforced region may refer to an upper head support portion of the elastic panel configured to support an upper head portion of the patient. However, the elastic panel may comprise a plurality of reinforced regions. For instance, the elastic panel may comprise in addition to the neck support portion a further reinforced region configured to support the upper head of the patient (i.e. the upper head support portion).

Generally, the term "more stretchable" may mean that with the same force exerted on the middle region and the at least one reinforced region, the elastic panel is stretched and/or elongated more, e.g. by a greater length, in the middle region than in the at least one reinforced region. Likewise, to stretch and/or elongate the middle region by the same length as the at least one reinforced region, a higher force needs to be exerted on the at least one reinforced region than on the middle region.

The middle region being more stretchable than the at least one reinforced region may be particularly advantageous for the following reasons. As a shape and/or weight of the neck and/or head and therefore the pressure onto the elastic panel may vary in certain regions, portions or areas of the elastic panel, it may be favoured or advantageous that an elongation or stretching behaviour of the elastic panel varies and/or differs in these regions, portions or areas of the elastic panel. This may ensure a tight fit of the elastic panel throughout the part of the neck and/or head which is in contact with the elastic panel. Different stretchabilities or elastic properties of the elastic panel in different regions, areas or portions thereof can also influence the patient's horizontal alignment. By way of example, in the middle head support portion of the elastic panel that supports the middle head having the largest circumference, it may be favoured that the elastic panel allows more stretch than in areas or portions, where the circumference of the head and/or neck is smaller. For instance, the neck support portion of the elastic panel that supports a part of the neck and/or the upper head support portion that supports the upper head may advantageously exhibit less elongation than in the middle head support portion that supports the middle head. This may ensure that the elastic panel encloses, encompasses and/or surrounds as much surface of the head and neck as possible, thereby increasing an efficiency and effectiveness of the immobilization, while also improving comfort for the patient.

Apart from that, by means of the different stretchabilities and/or the elastic properties in the middle region and the at least one reinforced region, an overall supported load as well as a load distribution over the headrest's length and/or width can be taken into account. For example, the load or force exerted onto the neck support region (i.e. the at least one reinforced region) of the elastic panel may be higher than in the middle region of the elastic panel, because in the neck support region a weight of the neck, part of the head and at least part of the shoulders may be absorbed. Hence, the at least one reinforced region may refer to a region of the elastic panel configured to support a portion of the head and neck having a smaller circumference than the middle head portion of the head and/or configured to support a region of the head and neck exerting more force or pressure onto the elastic panel than the middle head portion.

According to an embodiment of the present invention, a material thickness of the elastic panel in the middle region is smaller than a material thickness of the elastic panel in the at least one reinforced region. Alternatively or additionally the elastic panel comprises a first material in the middle region and a second material in the at least one reinforced region, the first material being different from the second material such that the middle region is more stretchable than the at least one reinforced region. Hence, the first material may be more stretchable than the second material. Accordingly, the thickness of the elastic panel can be adapted according to the desired elastic properties, stretchabilities, and/or deformation characteristics, e.g. the elastic panel can be thinner in areas, regions or portions being more stretchable, such as the middle region, and thicker and/or reinforced in areas, regions or portions being less stretchable, such as the at least one reinforced region, the neck support region and/or the upper head support portion. Accordingly, the thickness of the elastic panel can vary along the longitudinal axis of the headrest, e.g. over the length of the panel. Moreover, the thickness of the elastic panel can be even or homogenous over the whole width of the panel or vary within the panel width. Further, the thickness of the elastic panel may vary, i.e. decrease or increase, constantly or homogenously over the width and/or length of the elastic panel. Alternatively, the thickness of the elastic panel may vary, i.e. decrease or increase, inhomogenously over the width and/or length of the elastic panel. Hence, material thickness and/or elastic properties of the elastic panel can be inhomogenous throughout the elastic panel, i.e. along the longitudinal and/or transverse axis of the elastic panel. Further, changes in thickness and/or elastic properties can be continuous or discontinuous throughout the elastic panel, i.e. along the longitudinal and/or transverse axis of the elastic panel.

According to an embodiment of the present invention, the elastic panel comprises a first perforation pattern in the middle region and a second perforation pattern in the at least one reinforced region, wherein the first perforation pattern is different from the second perforation pattern, such that the middle region is more stretchable than the at least one reinforced region. For instance, a density of the elastic panel, i.e. a mass per unit volume, may be less in the middle region than in the at least one reinforced region, such that the middle region is more stretchable than the at least one reinforced region.

According to an embodiment of the present invention, the elastic panel comprises an elastic sheet arranged in the middle region and in the at least one reinforced region of the elastic panel, wherein the elastic panel comprises at least one further elastic sheet arranged only or solely in the at least one reinforced region of the elastic panel. In other words, the at least one further elastic sheet may not be arranged in the middle region. Accordingly, the at least one reinforced region of the elastic panel may be reinforced by means of the at least one further elastic sheet, wherein the elastic sheet and the at least one further elastic sheet may be arranged and/or run substantially parallel to each other. The elastic panel may also comprise two further elastic sheets, e.g. one arranged in the neck support portion and one arranged in the upper head support portion of the elastic panel to reinforce these regions or portions of the elastic panel. Apart from that, the elastic sheet may have a greater length than the at least one further elastic sheet. Alternatively or additionally, the elastic sheet may differ from the at least one further elastic sheet, e.g. in terms of stretchability, elasticity and/or material, such that the at least one reinforced region, in which the at least one further elastic sheet is arranged, is less stretchable than the middle region of the elastic panel.

According to an embodiment of the present invention, the elastic panel comprises at least one stiffening rib arranged in the at least one reinforced region. In other words, the at least one reinforced region of the elastic panel may be reinforced and/or stiffened by means of the at least one stiffening rib. Also, a plurality of stiffening ribs may be arranged in the at least one reinforced region. The at least one stiffening rib may comprise the same or a different material than remaining or other parts of the elastic panel. Accordingly, also the stiffening rib may be stretchable, reversibly stretchable, reversibly deformable and/or elastic. The at least one stiffening rib may have the same or a different thickness as remaining or other parts of the elastic panel. The at least one stiffening rib may extend in an arbitrary direction, e.g. substantially parallel to the transverse axis or the longitudinal axis of the elastic panel. The at least one stiffening rib may be attached, e.g. glued or fused, to the at least one reinforced region of the elastic panel or it may not be coupled or attached to the at least one reinforced region.

According to an embodiment of the present invention, the at least one stiffening rib is integrally formed with an elastic sheet of the elastic panel. Such integral formation may simplify operation of the headrest, e.g. in terms of a handling or cleaning of the headrest. By way of example, the at least one stiffening rib may be integrated onto an elastic sheet of the elastic panel (e.g. a main elastic sheet) or it may be integrated onto a further elastic sheet.

According to an embodiment of the present invention, the at least one reinforced region is arranged on a first end of the elastic panel. The first end may denote an end of the elastic panel along the longitudinal axis of the elastic panel. As described above, the at least one reinforced region may refer to a neck support portion that is arranged on the first end of the elastic panel.

According to an embodiment of the present invention, the elastic panel comprises a first reinforced region on a first end of the elastic panel and a second reinforced region arranged on a second end of the elastic panel opposite to the first end of the elastic panel along the longitudinal axis of the elastic panel, wherein the middle region is arranged and/or interposed between the first reinforced region and the second reinforced region along a longitudinal axis of the elastic panel. The first reinforced region may denote the neck support portion of the elastic panel and the second reinforced region may denote the upper head support portion, as described above.

According to an embodiment of the present invention, the headrest further comprises at least one shaping support coupled with a first end of the shaping support to the supporting structure, wherein a second end of the at least one shaping support protrudes and/or extends from the supporting structure towards a centre portion of the headrest. The at least one shaping support may be detachably coupled to the supporting structure. For instance, different shaping supports may be used for different patients or different head and neck sizes. Alternatively, the at least one shaping support may be fixed to the supporting structure and/or the at least one shaping support may be integrally formed with the supporting structure. Accordingly, the at least one shaping support may be formed as separate part which is attached to the supporting structure or it may be fully integrated therein. Also, the supporting structure itself may form the at least one shaping support.

Generally, the at least one shaping support may be solid, rigid and/or dimensionally stable. Alternatively, at least a part of the at least one shaping support may be flexible and/or bendable, such that it can bend into a direction of the force exerted by the patient's head and/or neck.

The at least one shaping support may be particularly advantageous for the following reasons. In areas, regions and/or portions of the elastic panel that are configured to support a part of the head and/or neck that has a smaller circumference than other parts of the head and/or neck, such as e.g. the neck portion or the upper head portion of the patient, a tight fit of the elastic panel can be enforced with the at least one shaping support, which can prevent the elastic panel from stretching downwards, e.g. in direction of the force exerted by the patient, and not embracing the body. This is particularly the case in the neck support region of the elastic panel. To achieve this, the shaping support may extend and/or protrude towards the center portion of the headrest, e.g. along the transverse axis over at least about 1%, for example at least about 3%, preferably at least about 5%, more preferably at least about 10% and even more preferably at least about 15% of the width of the elastic panel measured along the transverse axis. Thereby, a distance between the surface of the patient and an edge (or the second end) of the shaping support can be decreased, wherein the edge of the shaping support may support the elastic panel, such that the elastic panel between the shaping support and the patient's surface stretches less in a direction of the force exerted by the patient, but rather tightly encloses the patient's surface.

According to an embodiment of the present invention, a contour of at least a part of the second end or an edge of the at least one shaping support is curvedly or curvilinear formed. Alternatively or additionally, a contour of at least a part of the second end or an edge of the at least one shaping support is formed corresponding to a contour of at least a part of the head and/or neck of the patient. Accordingly, the second end or the edge of the shaping support that is directed towards the centre portion of the headrest may be anatomically shaped. Also, the shaping support may have a three-dimensional shape or form that corresponds to the patient's anatomy or shape. By way of example, the at least one shaping support may be arranged in proximity to the neck support region of the elastic panel. Accordingly, the second end or edge of the shaping support may be formed or shaped in correspondence with the contour or shape of the patient in the neck portion of the patient. Alternatively or additionally the at least one shaping support may be arranged in proximity of the upper head support portion and/or the middle head support portion, and the second end or edge may be formed in correspondence with the contour or shape of the patient in these regions. Also, the shaping support may be head and/or neck like formed, such that the shaping support may surround at least a part of the head and/or neck along a circumference thereof, e.g. in a plane through the patient's ears.

According to an embodiment of the present invention, at least a part of the at least one shaping support is plate-like formed. Such plate-like shaping support may be cost-efficiently manufactured. Also, the plate-like shaping support may be manufactures relatively thin, such that only a small amount of radiation may be absorbed therein, particularly in an anterior-posterior direction.

According to an embodiment of the present invention, at least a part of the elastic panel is attached, coupled and/or fixed to the at least one shaping support. For instance, the elastic panel may be attached to the second end or edge of the shaping support. Alternatively or additionally, at least a part of the elastic panel is arranged on top of the at least one shaping support. Accordingly, at least a part of the elastic panel may be attached to the supporting structure and run or extend over or on top of the shaping support.

According to an embodiment of the present invention, at least a part of the at least one shaping support is flexible and/or bendable. Particularly, the shaping support may be flexible and/or bendable near the second end or edge thereof. This may allow usage of the headrest for many different patients with largely different sizes and/or shapes of the head or neck. Also, a comfort may be improved for the patient.

According to an embodiment of the present invention, the at least one shaping support comprises a solid portion arranged on the first end of the shaping support and a flexible portion arranged on the second end of the shaping support. This allows the shaping support to be bend at the second end, while increasing robustness by means of the solid portion. Also, the solid portion may further ensure that the elastic panel tightly fits or encloses the patient's surface.

Generally, the shaping support may be more flexible or bendable near or at the second end than near or at the first end. To achieve this, e.g. a cross-section, a thickness, a dimension and/or a material may differ at the respective ends of the shaping support. Accordingly, the first end or solid portion may be thicker or comprise a less flexible material than the second end or flexible portion of the shaping support, so that it allows less bend close to the supporting structure and more bend close to the patient's body or the center portion of the headrest.

According to an embodiment of the present invention, the headrest comprises a first shaping support arranged on a first side of the supporting structure and a second shaping support arranged on a second side of supporting structure opposite to the first side of the supporting structure. Accordingly, the centre region of the headrest and/or the patient may be arranged between the first shaping support and the second shaping support, e.g. such that the first and second shaping supports at least partly encompass the patient's neck and/or head.

According to an embodiment of the present invention, the supporting structure comprises a first rail coupled to a first side of the elastic panel and a second rail coupled to a second side of the elastic panel opposite to the first side of the elastic panel. The first rail may be arranged on a first side of the elastic panel and the second rail may be arranged on a second side of the elastic panel opposite the first side, such that the elastic panel is at least partly arranged and/or interposed between the first rail and the second rail. The first rail and/or the second rail may be configured to be coupled to another part or component of the immobilization system, such as e.g. a base of a mask or thermoplastic mask. Accordingly, the first rail and/or the second rail may comprise corresponding interfaces for mechanically coupling one or both of them to another part or component of the immobilization system. The supporting structure may also comprise one or more further rails, e.g. surrounding the elastic panel on one or more further sides thereof. Accordingly, the supporting structure may form a frame or frame-like structure for the elastic panel.

According to an embodiment of the present invention, the supporting structure comprises a frame element at least partly surrounding the elastic panel on at least three sides of the elastic panel. This may allow to hold the elastic panel in place in a stable and robust manner. By way of example, the frame element may be rectangular shaped, U-shaped and/or trapezoidal shaped.

The present invention also relates to a use of a headrest, as described above and in the following, in an immobilization system for immobilizing, positioning and/or fixing at least a part of a patient.

According to a second aspect of the present invention, there is provided an immobilization system and/or a head immobilization system for immobilizing, positioning and/or fixing at least a part of a patient. The immobilization system comprises a headrest, as described above and in the following, for supporting at least a part of a head and/or neck of the patient, and an immobilization mask coupled to the headrest. Therein, the headrest and the immobilization mask together form a compartment configured to receive, encompass, surround and/or enclose at least a part of the head and/or neck of the patient. By way of example, the immobilization mask may comprise thermoplastic material, which can be individually adapted or formed in a heated condition according to the patient's head, fore head and/or face, such that, after the thermoplastic has cooled down and cured, the mask tightly fits to the head of the patient. The immobilization mask can be attached and/or mechanically coupled to the headrest, particularly to the supporting structure of the headrest, e.g. by means of a bolt connection, a clamp connection or any other suitable connection.

The immobilization system may particularly be configured for immobilizing a patient's head in a supine position of the patient. The system may comprise a support rail structure configured to be coupled to a patient rest, e.g. a patient bed, and extending at least on both lateral sides of the patient's head. The headrest, particularly the supporting structure may be coupled to the support rail structure. The system may further comprise a mask frame or mask base configured to be coupled to at least one deformable upper mask sheet, wherein the mask frame may be releasably connected to the support rail structure via a first interface section and a second interface section, with at least two pins protruding from the first interface section in a first direction, and at least two pin-receptions provided at the second interface section, wherein each one of the pin-receptions may receive one of the pins. The system may further comprise a catch-mechanism for each pin-reception and each corresponding pin, which allows the pin to be pushed further into the pin-reception in the first direction, but which interlocks in case of an attempted withdrawal of the pin from the pin-reception in a second, opposite direction.

According to a third aspect of the invention there is provided a method of immobilizing at least a part of a head and/or a neck of a patient. The method comprising the steps of:

providing a headrest, as described above and in the following; and arranging at least a part of the head and/or at least a part of the neck of the patient on the elastic panel of the headrest, such that at least a part of the elastic panel is stretched and abuts and/or encloses at least a part of the head and/or neck of the patient, thereby at least partly immobilizing the head and/or neck of the patient.

It is emphasized that features, functions, elements and/or steps, which are described above and in the following with reference to one aspect of the invention, equally apply to any other aspect of the invention described above and in the following. Particularly, features, functions and/or elements, as described above and in the following with reference to the headrest according to the first aspect, equally apply to the immobilization system according to the second aspect and/or to the method according to the third aspect, and vice versa.

These and other aspects of the invention will be apparent from and elucidated with reference to the embodiments described hereinafter.

BRIEF DESCRIPTION OF THE DRAWINGS

In the following, the invention is described with reference to the appended figures which give background explanations and represent exemplary embodiments of the invention. The scope of the invention is however not limited to the specific features disclosed in the context of the figures, wherein FIGS. 1A and 1B each show a perspective view of a headrest according to an exemplary embodiment of the invention;

FIGS. 4A and 4B each show a perspective view of a headrest according to another exemplary embodiment of the invention;

FIGS. 5A to 6B each show a cross-sectional view of a headrest according to exemplary embodiments of the invention;

The figures are schematic only and not true to scale. In principle, identical or like parts, elements and/or steps are provided with identical or like reference symbols in the figures.

DESCRIPTION OF EMBODIMENTS

Figure 1A:
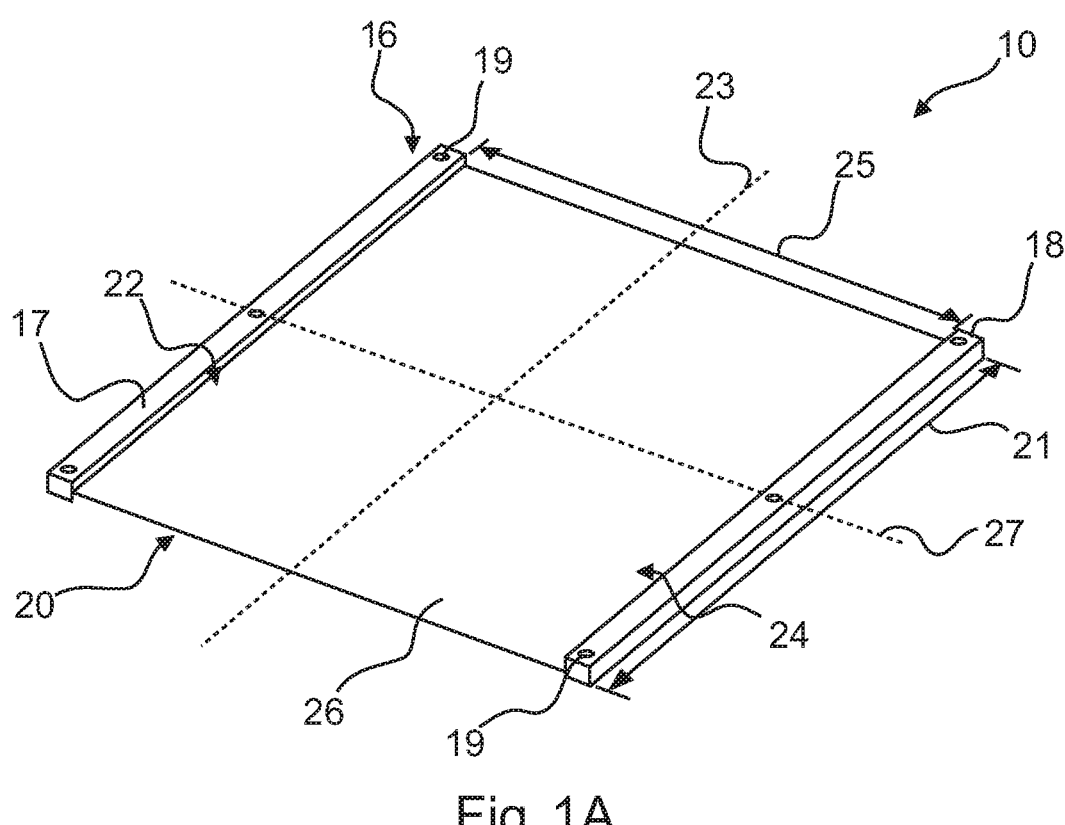
Figure 1B:
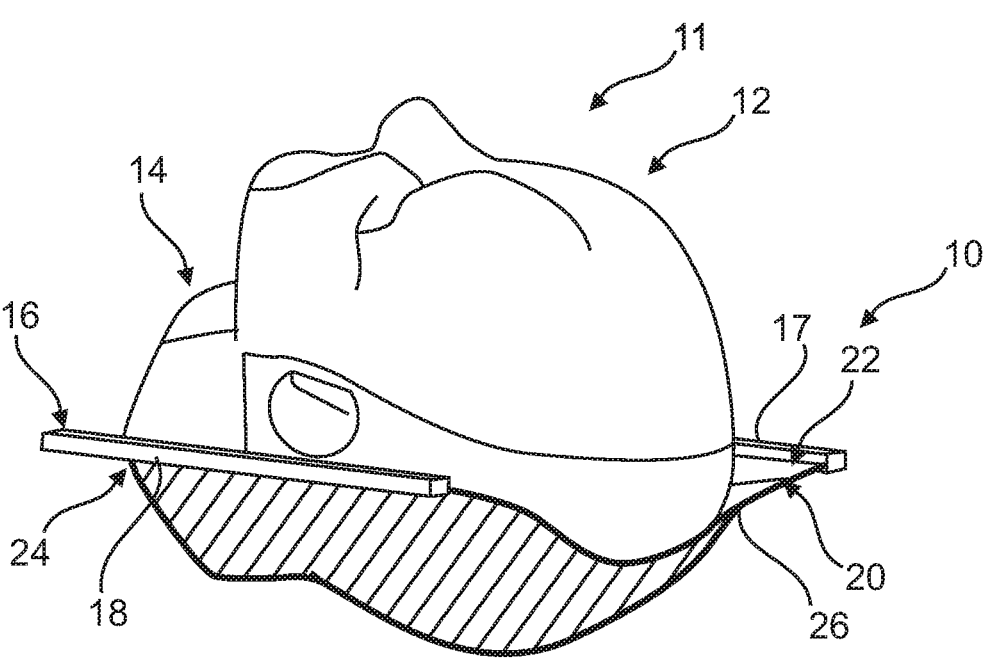

FIGS. 1A and 1B each show a perspective view of a headrest 10 for immobilizing, positioning and/or fixing at least a part of a head 12 and/or at least a part of a neck 14 of a patient 11 according to an exemplary embodiment of the invention. Therein, the headrest 10 is depicted in a rest position in FIG. 1A, in which no force is exerted by the patient 11 onto the headrest 10. FIG. 1B shows the headrest 10 in use, i.e. in a configuration where the at least part of the head 12 and/or neck 14 rests on the headrest 10.

The headrest 10 comprises a supporting structure 16 and a sheet-like formed elastic panel 20 attached to the supporting structure 16. In the example depicted in FIGS. 1A and 1B, the supporting structure 16 comprises a first rail 17 and a second rail 18. A first side 22 of the elastic panel 20 is coupled, attached and/or fixed to the first rail 17 and a second side 24 of the elastic panel 20 opposite to the first side 22 is attached, coupled and/or fixed to the second rail 18 such that the elastic panel 20 is arranged between and/or held in place by the first and second rails 17, 18. The elastic panel 20 may be attached by any appropriate connection to the supporting structure 16, such as e.g. a glue connection, a clamp connection or the like.

The supporting structure 16 and/or the first and second rails 17, 18 are manufactured from dimensionally stable, rigid or solid material, such as e.g. plastic material, hard plastic, composite material, reinforced plastic or any other suitable material. The supporting structure 16 is configured to be attached and/or coupled to other components or elements of an immobilization system 100 (see FIG. 11). For this purpose, the support structure 16 comprises appropriate coupling means 19 or interfaces 19.

The sheet-like formed elastic panel 20 of FIGS. 1A and 1B comprises a single elastic sheet 26 that is membrane-like or foil-like formed. Accordingly, a thickness of the elastic sheet 26 and/or the elastic panel 20 is smaller than a length 21 and/or a width 25 of the elastic panel 20 and/or the elastic sheet 26. Therein, the length 21 is measured along a longitudinal axis 23 of the headrest 10 or panel 20 that extends substantially parallel to the first and second rails 17, 18. Further, the width 25 is measured along a transverse axis 27 of the headrest 10 or panel 20 extending between the first and second rails 17, 18. Further, the thickness of the sheet-like elastic panel 20 and/or the elastic sheet 26 is measured transverse or perpendicular to both the transverse axis 27 and the longitudinal axis 23. By way of example, the thickness of the elastic panel 20 or sheet 26 may be less than about 10%, particularly less than about 5%, preferably less than about 3%, and even more preferably less than about 1% of the width 25 and/or length 21 of the elastic panel 20 or sheet 26. For instance, the thickness of the elastic panel 20 or sheet 26 may range from about 0.1 mm to 5 cm, e.g. from about 0.1 mm to about 2 cm, preferably from about 0.2 mm to about 0.5 cm, and more preferably from about 0.3 mm to about 3 mm.

The elastic panel 20 and/or the elastic sheet 26 comprises elastic material, such as e.g. polymer-based elastic material, elastomer, rubber, elastic foam and/or silicon. Specifically, the elastic panel 20 and/or the elastic sheet 26 is reversibly deformable and/or reversibly stretchable at room temperature, e.g. ranging from about 15° C. to about 35° C.

The elastic panel 20 and/or the elastic sheet 26 is configured to support at least a part of the patient's 11 head 12 and/or neck 14, as illustrated in FIG. 1B. Under or in response to a force exerted by the patient's 11 head 12 and/or neck 14, the elastic panel 20 and/or the elastic sheet 26 stretches and/or elongates, such that a shape of at least a part of the elastic panel 20 and/or sheet 26 is formed in correspondence or corresponding to a shape, form or anatomy of the head 12 and/or neck 14, as shown in FIG. 1B. Due to this stretchability of the elastic panel 20 and/or sheet 26 at least a part of the panel 20 and/or sheet 26 encloses, particularly tightly encloses, or abuts a part of the head 12 and/or neck 14, thereby at least partly immobilizing the head 12 and/or neck 14 of the patient 11. When the patient 11 places its head 12 and/or neck 14 onto the elastic panel 20, the length 21 and/or the width 25 of the elastic panel 20 and/or sheet 26 is increased and/or elongated with respect to the rest position by at least 1%, e.g. by at least 5%, preferably by at least 10%, more preferably by at least 30%, and even more preferably by at least 50%. When the force exerted by the patient 11 onto the elastic panel 20 is removed, the elastic panel 20 resumes its original size and shape, i.e. it resumes the rest position as shown in FIG. 1A.

Figure 2:
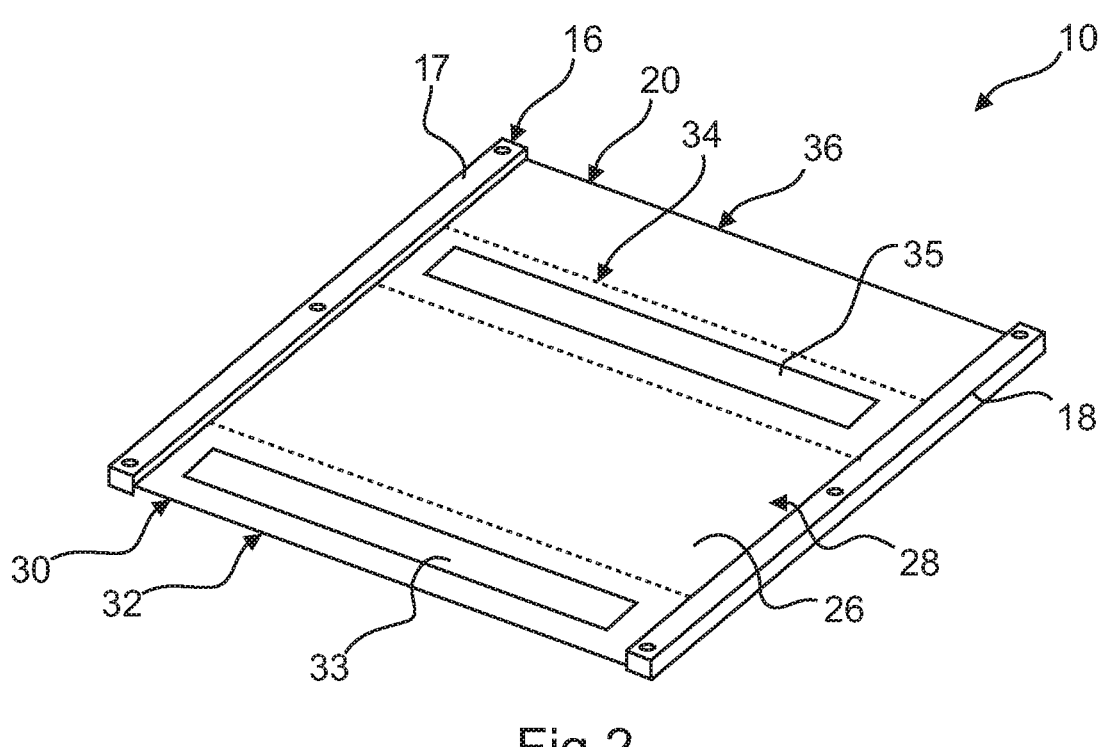
FIG. 2 shows a perspective view of a headrest according to another exemplary embodiment of the invention.

FIG. 2 shows a perspective view of a headrest 10 according to another exemplary embodiment of the invention. If not stated otherwise, the headrest 10 of FIG. 2 comprises the same features, elements and/or functions as the headrest 10 of FIGS. 1A and 1B.

The elastic panel 20 of the headrest 10 of FIG. 2 comprises a middle region 28 configured to support a middle head of the patient 11, wherein the middle head refers to a portion of the head 12 having the largest circumference compared to other portions of the head 12 or neck 14. Accordingly, the middle region 28 may refer to a middle head support portion 28 of the headrest 10 or elastic panel 20.

The elastic panel 20 further comprises a first reinforced region 30 arranged at a first end 32 of the elastic panel 20 and a second reinforced region 34 arranged at a second end 36 of the elastic panel 20 opposite to the first end 32 along the longitudinal axis 32. The first and second ends 32, 36 refer to ends or end portions of the elastic panel 20 along the longitudinal axis 23. Accordingly, the middle region 28 is arranged between the first reinforced region 30 and the second reinforced region 34 of the elastic panel 20. Generally, the first reinforced region 30 may refer to a neck support portion 30 of the elastic panel 20 configured to support at least a part of the neck 14. Further, the second reinforced region 34 may refer to an upper head support portion 34 of the elastic panel 20 configured to support an upper head of the patient 11. It is emphasized, however, that the headrest 10 may alternatively comprise only one of the first and second reinforced regions 30, 34 or the elastic panel 20 may comprise more than the first and second reinforced regions 30, 34.

By means of the first and second reinforced regions 30, 34 it may be taken into account, that a load, pressure or force exerted by the patient 11 in one of those regions 30, 34 and/or a circumference of the head 12 or neck 14 may differ with respect to the middle region 28 supporting the middle head. Specifically, a force exerted on the first reinforced region 30 can be larger than a force exerted on the middle region 28. Also, a circumference of the neck 12 usually is smaller than a circumference of the middle head. Likewise, a circumference or the upper head usually is smaller than a circumference of the middle head.

In order to ensure that the elastic panel 20 tightly encloses as much surface of the patient 11 as possible, the first and second reinforced regions 30, 34 are less stretchable than the middle region 28 of the elastic panel 20. To achieve this, for instance a thickness or material thickness of the elastic panel 20 in the first and second reinforced regions 30, 34 may be thicker than a thickness or material thickness of the elastic panel 20 in the middle region 28. Therein, the thickness can be even over the whole width 25 of the elastic panel 20 or it can vary within the width 25 of the elastic panel 20.

Further, if the thickness varies it can decrease or increase constantly or inhomogenously throughout the width 25 of the panel 20. For example, the thickness may gradually or constantly increase from the first rail 17 to a center of the panel 20 and then decrease gradually or constantly from the center of the panel 20 to the second rail 18.

Alternatively or additionally the elastic panel 20 may comprise a less stretchable or less elastic material in the reinforced regions 30, 34 compared to a material of the elastic panel 20 in the middle region 28.

In the example depicted in FIG. 2, the elastic panel 20 comprises a first stiffening rib 33 arranged in the first reinforced region 30 and a second stiffening rib 35 arranged in the second reinforced region 34. By means of the stiffening ribs 33, 35, a material thickness of the elastic panel 20 is increased with respect to the middle region 28 and a stretchability is decreased with respect to the middle region 28.

The stiffening ribs 33, 35 depicted in FIG. 2 extend substantially parallel to the transverse axis 27 between the first and second rails 17, 18 and have a smaller width than the elastic panel 20. However, the width of the stiffening ribs 33, 35 may alternatively equal the width 25 of the elastic panel 20. The stiffening ribs 33, 35 may be integrated onto the elastic panel 20 and/or the elastic sheet 26, or the stiffening ribs 33, 35 may be formed as separate parts and e.g. fixed on two opposite sides to the first and second rail 17, 18, respectively. One or both of the stiffening ribs 33, 35 may be arranged on a side or surface of the elastic panel 20 that is in contact with the patient 11. Alternatively, one or both of the stiffening ribs 33, 35 may be arranged on a side or surface of the elastic panel 20 opposite to the side or surface that is in contact with the patient 11. Also, one stiffening rib 33, 35 may be arranged on the side or surface that is in contact with the patient 11 and the other one of the stiffening ribs 33, 35 may be arranged on the opposite side or surface.

Further, the stiffening ribs 33, 35 may comprise the same material as the elastic sheet 26 or they may comprise a different material.

Alternatively or additionally, the elastic panel 20 may comprise a first perforation pattern in the middle region 28 and a second perforation pattern in the reinforced regions 30, 34 that is different from the first perforation pattern, such that the middle region 28 is more stretchable than the reinforced regions 30, 34.

Figure 3A:
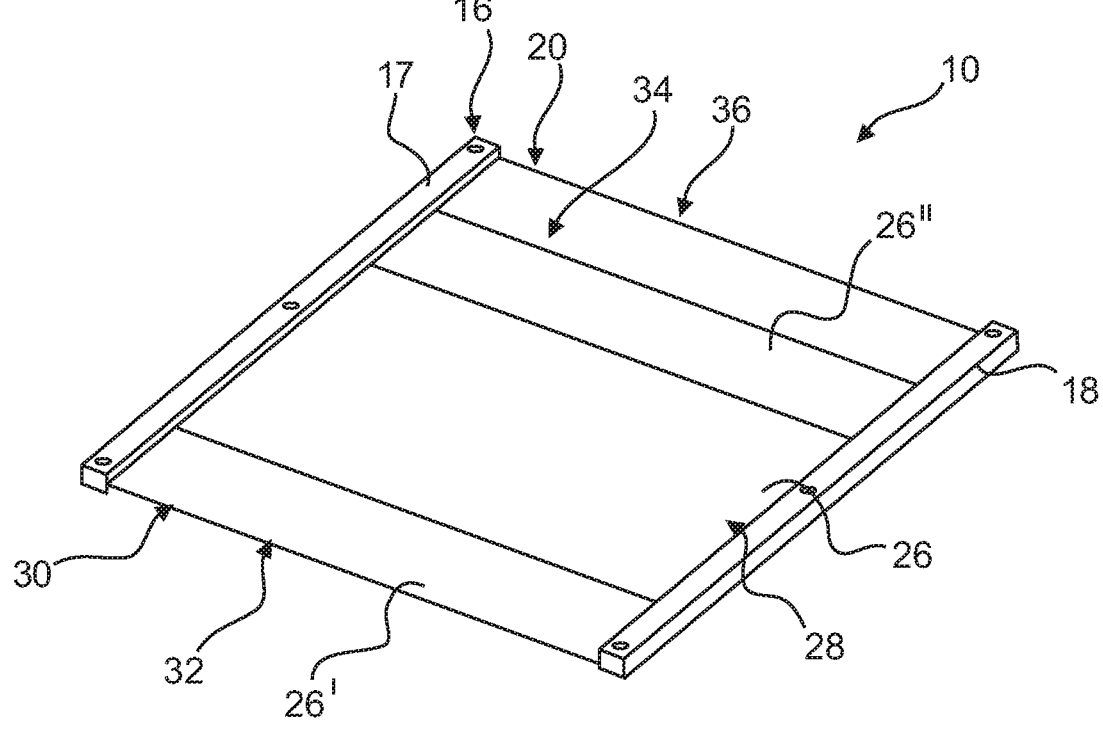
FIGS. 3A and 3B each show a perspective view of a headrest according to another exemplary embodiment of the invention.
Figure 3B:
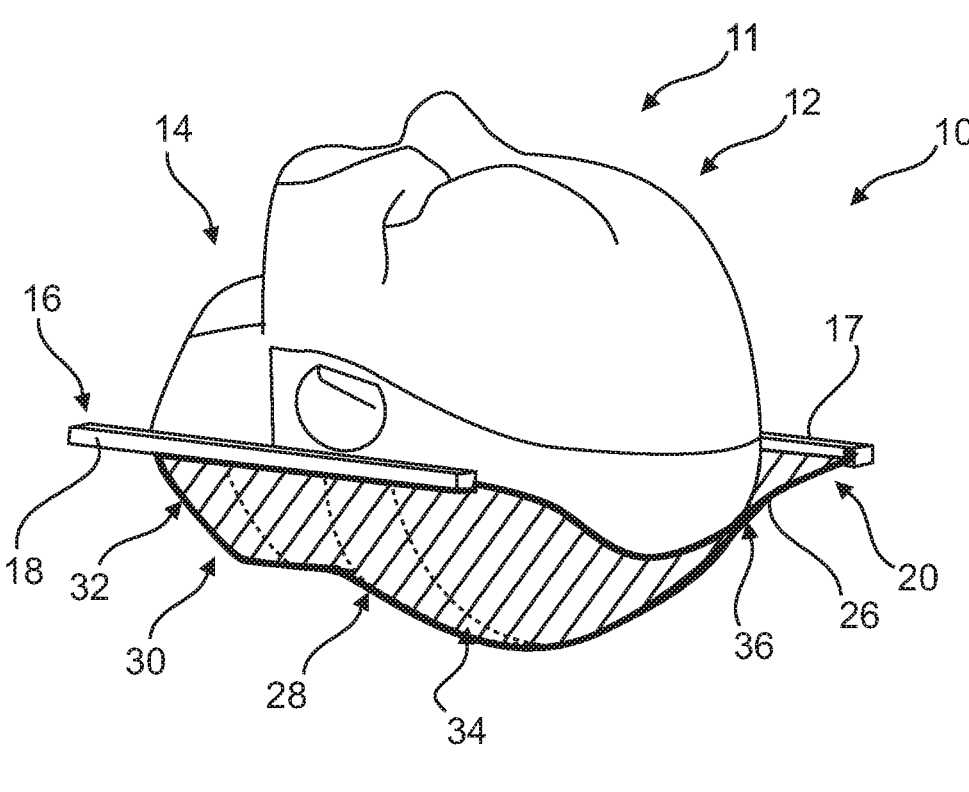

FIGS. 3A and 3B each show a perspective view of a headrest 10 according to another exemplary embodiment of the invention. If not stated otherwise, the headrest 10 of FIGS. 3A and 3B comprises the same features, elements and/or functions as the headrests 10 described with reference to the previous figures.

In the embodiment depicted in FIGS. 3A and 3B, the elastic panel 20 comprises an elastic sheet 26 that extends over the whole length 21 of the elastic panel 20 from the first reinforced region 30 over the middle region 28 and the second reinforced region 34. Therein, the elastic sheet 26 may refer to a main elastic sheet 26 of the elastic panel 20.

The elastic panel 20 comprises a first further elastic sheet 26' arranged only in the first reinforced region 30, such that the elastic panel 20 is less stretchable in this region 34 compared to the middle region 28. The elastic panel 20 comprises a second further elastic sheet 26" arranged only in the second reinforced region 34, such that the elastic panel 20 is less stretchable in the second reinforced region 34 compared to the middle region 28.

The first and second further elastic sheets 26', 26" both extend over the whole width 25 of the elastic panel 20 but have shorter lengths compared to the elastic sheet 26. The first and second further elastic sheets 26', 26" may be attached to the elastic sheet 26 or not. The first and second further elastic sheets 26' 26" may comprise the same material as the elastic sheet 26 or they may comprise different material, e.g. a less stretchable material. One or both of the first and second further elastic sheets 26', 26" may be arranged on a side or surface of the elastic panel 20 that is in contact with the patient 11. Alternatively, one or both of the first and second further elastic sheets 26', 26" may be arranged on a side or surface of the elastic panel 20 opposite to the side or surface that is in contact with the patient 11. Also, one of the first and second further elastic sheets 26', 26" may be arranged on the side or surface that is in contact with the patient 11 and the other one of the first and second further elastic sheets 26', 26" may be arranged on the opposite side or surface. Accordingly, one or both of the first and second further elastic sheets 26', 26" may be in contact with the patient 11.

As illustrated in FIG. 3B, by means of the first and second reinforced regions 30, 34 it can be ensured that the elastic panel 20 tightly encloses the upper head and the neck 14 of the patient, while the middle region 28 of the elastic panel 20 allows enough stretch such that the middle region 28 tightly encloses the middle head of the patient 11. This way, the head 12 and/or neck 14 may be effectively held in place, positioned, immobilized and/or fixed with the headrest 10.

Figure 4A:
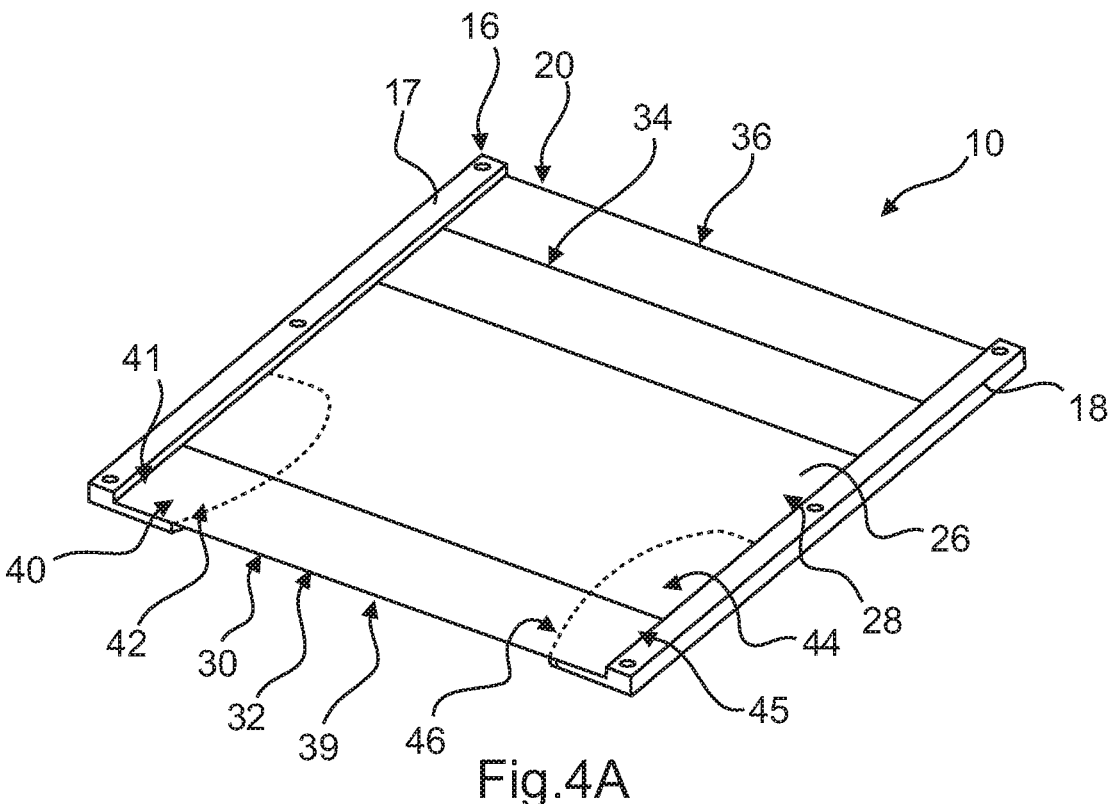
Figures 4B, 5A, 5B, 6A, 6B:
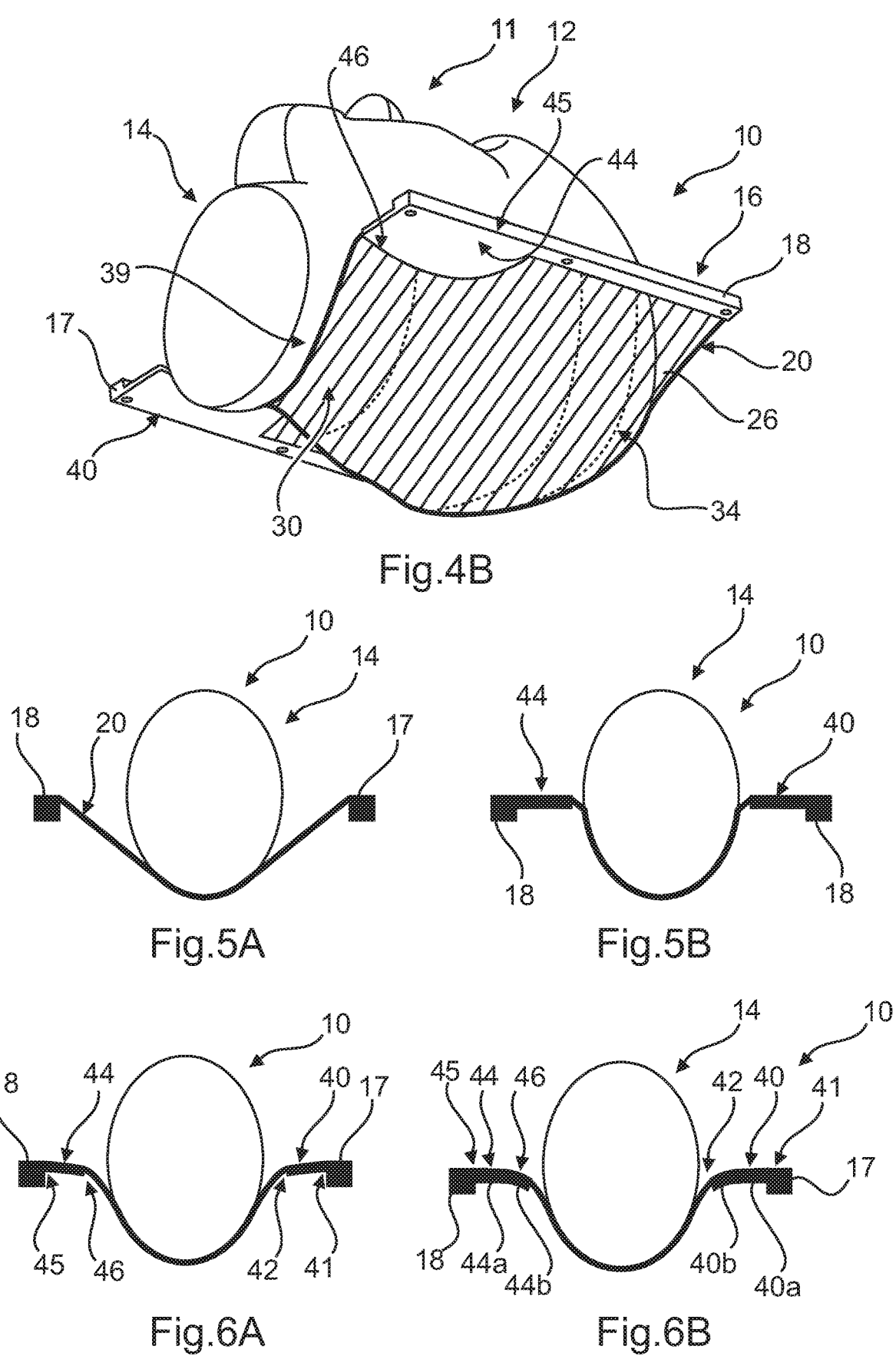

FIGS. 4A and 4B each show a perspective view of a headrest 10 according to another exemplary embodiment of the invention. If not stated otherwise, the headrest 10 of FIGS. 4A and 4B comprises the same features, elements and/or functions as the headrests 10 described with reference to the previous figures.

The headrest 10 depicted in FIGS. 4A and 4B comprises a first shaping support 40 attached with a first end 41 thereof to the first rail 17, wherein a second end 42 or edge 42 of the first shaping support 40 extends and/or protrudes substantially parallel to the elastic panel 20 towards a center portion 39 or center 39 of the elastic panel 20.

The headrest 10 comprises a second shaping support 44 attached with a first end 45 thereof to the second rail 18, wherein a second end 46 or edge 46 of the second shaping support 44 extends and/or protrudes substantially parallel to the elastic panel 20 towards the center portion 39 or center 39 of the elastic panel 20. Both the first and the second shaping supports 40, 44 are arranged symmetrically with respect to the longitudinal axis 23 and are arranged proximate or at the first end 32 of the headrest 10 or elastic panel 20.

In the example depicted in FIGS. 4A and 4B, the first and second shaping supports 40, 44 are substantially plate-like formed and the elastic panel 20 is arranged on top of or runs over the first and second shaping support 40, 44, respectively. Alternatively, the first and second shaping supports 40, 44 may be arranged on top of the elastic panel 20, such that the elastic panel 20 may run beneath the first and second shaping supports 40, 44. Alternatively, the elastic panel 20 can be attached and/or fixed to the second end 42 or edge 42 of the first shaping support 40 and to the second end 46 or edge 46 of the second shaping support 44.

The first and second shaping supports 40, 44 are integrally formed with the supporting structure 16. However, the shaping supports 40, 44 may also be attached and/or detachably attached to the supporting structure 16.

Generally, the shaping supports 40, 44 may be solid, rigid and/or dimensionally stable. Alternatively, at least a part of the shaping supports 40, 44 may be flexible and/or bendable, as will be further discussed with reference to FIGS. 5A to 6B.

In areas, regions and/or portions of the elastic panel 20 that are configured to support a part of the head 12 and/or neck 14 that has a smaller circumference or diameter than other parts of the head 12, such as e.g. the neck portion, a tight fit of the elastic panel 20 to the patient's surface can be enforced with the first and second shaping supports 40, 44, which can prevent the elastic panel 20 from stretching downwards, e.g. in direction of the force exerted by the patient 11, and not embracing the body, as will be further elucidated in FIGS. 5A and 5B. To achieve this, the first and second shaping supports 40, 44 may extend and/or protrude towards the center portion 39 of the headrest, e.g. along the transverse axis 27, over at least about 1%, for example at least about 3%, preferably at least about 5%, more preferably at least about 10% and even more preferably at least about 15% of the width 25 of the elastic panel measured along the transverse axis 27. Thereby, a distance between the surface of the patient 11 and the edges 42, 46 or second ends 42, 46 of the first and second shaping supports 40, 44, respectively, can be decreased, wherein the edges 42, 46 of the shaping supports 40, 44 support the elastic panel 20, such that the elastic panel 20 between the first and second shaping supports 40, 44 and the patient's surface, respectively, stretches less in a direction of the force exerted by the patient 11, but rather tightly encloses the patient's surface.

Further, the second end 42, 46 of each of the shaping supports 40, 44 is curved or curvilinear formed, thereby taking into account the anatomy of the patient 11 in proximity to the shaping supports 40, 44. In other words, the edges 42, 46 of the first and second shaping supports 40, 44 are formed in correspondence with the patient's anatomy.

Alternatively or additionally to the shaping supports 40, 44 arranged at the first end 32 of the elastic panel 20, i.e. in proximity to the neck 14, the headrest 10 may also comprise one or more further shaping supports, e.g. in proximity to the second end 36 of the elastic panel 20.

FIGS. 5A and 5B each show a cross-sectional view of a headrest 10 according to an exemplary embodiment of the invention. If not stated otherwise, the headrest 10 of FIGS. 5A and 5B comprises the same features, elements and/or functions as the headrests 10 described with reference to the previous figures. Specifically, FIGS. 5A and 5B show a cross-sectional view through the neck 14 of the patient 11 and the headrest 10, wherein the headrest 10 shown in FIG. 5A does not comprise shaping supports 40, 44, whereas the headrest 10 shown in FIG. 5B does comprise the shaping supports 40, 44 as described with reference to FIGS. 4A and 4B.

As shown in FIG. 5A, when the headrest 10 does not comprise the shaping supports 40, 44, the elastic panel 20 may predominantly stretch downwards, i.e. in direction of the force exerted by the patient 11 on to the elastic panel 20, wherein only a small part of the surface of the neck 14 may be in direct contact with the elastic panel 20.

In contrast, when the headrest 10 comprises the shaping supports 40, 44, as shown in FIG. 5B, it can be ensured that the elastic panel 20 covers, encloses and/or is in contact with a major part of the surface of the neck 14. Hence, such configuration may allow to more effectively immobilize, position and/or fix the patient 11 by means of the headrest 10.

FIGS. 6A and 6B each show a cross-sectional view of a headrest 10 according to an exemplary embodiment of the invention. If not stated otherwise, the headrest 10 of FIGS. 6A and 6B comprises the same features, elements and/or functions as the headrests 10 described with reference to previous figures. Similarly to FIGS. 5A and 5B, FIGS. 6A and 6B show a cross-section through the headrest 10 and the neck 14 of the patient 11.

In the embodiment depicted in FIG. 6A, the first shaping support 40 and the second shaping support 44 are flexible and/or bendable, such that both the first and the second shaping supports 40, 44 can bend downwards, i.e. in direction of the force exerted by the patient 11 onto the elastic panel 20. Therein, a cross-section and/or a thickness of the first shaping support 40 and the second shaping support 44 may be larger proximate or close to the first ends 45, 41 of the shaping supports 40, 44 compared to a cross-section or thickness of the shaping supports 40, 44 proximate or close to the second ends 42, 46, respectively. This may further improve a comfort for the patient 11. Also, this may allow that the headrest 10 can be used for patients 11 having largely different neck sizes.

In contrast to the embodiment depicted in FIG. 6A, in the embodiment illustrated in FIG. 6B, the first shaping support 40 comprises a solid portion 40a proximate or close to the first end 41 and a flexible portion 40b proximate or close to the second end 42. The solid portion 40a and the flexible portion 40b may be formed as a single part or as multiple parts. Likewise, the second shaping support 44 comprises a solid portion 44a proximate or close to the first end 45 and a flexible portion 44b proximate or close to the second end 46. The solid portion 44a and the flexible portion 44b may be formed as a single part or as multiple parts.

Figures 7, 8:
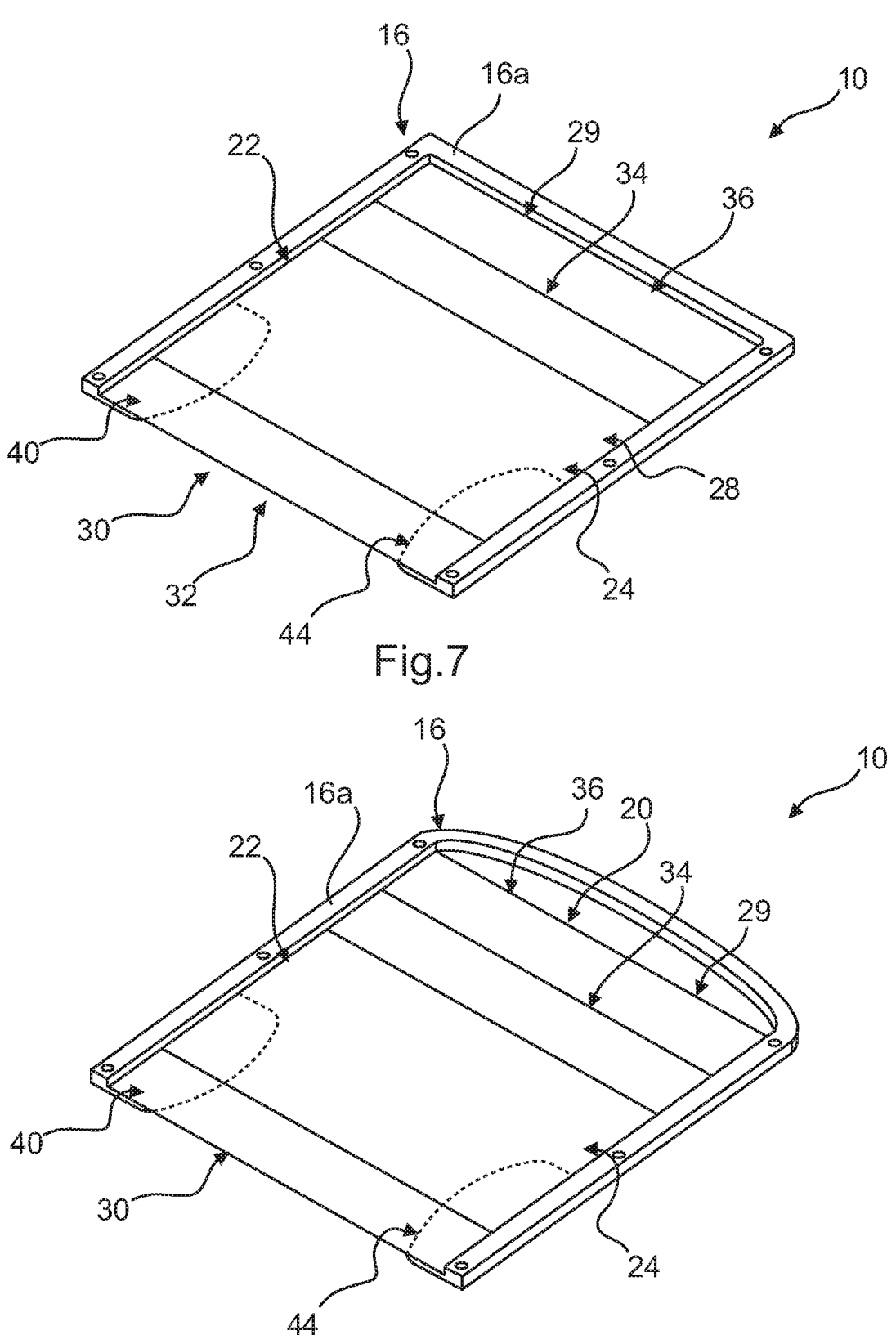
FIG. 7 shows a perspective view of a headrest according to another exemplary embodiment of the invention.
FIG. 8 shows a perspective view of a headrest according to another exemplary embodiment of the invention.

FIG. 7 shows a perspective view of a headrest 10 according to another exemplary embodiment of the invention. If not stated otherwise, the headrest 10 of FIG. 7 comprises the same features, elements and/or functions as the headrests 10 described with reference to the previous figures.

The headrest 10 depicted in FIG. 7 comprises a supporting structure 16 with a frame element 16a that at least partly surrounds the elastic panel 20 on three sides. The frame element 16a may be manufactured as a single part or as multiple parts. For instance, the frame element 16a may comprise three rails connected to each other, thereby forming the frame element 16a.

The frame element 16a depicted in FIG. 7 is substantially rectangular shaped. The elastic panel 20 is attached to the frame element 16a at least on the first side 22 and the second side 24 thereof. Optionally, the elastic panel 20 may also be attached to the frame element 16a on a side 29 at the second end 36 of the elastic panel 20.

FIG. 8 shows a perspective view of a headrest 10 according to another exemplary embodiment of the invention. If not stated otherwise, the headrest 10 of FIG. 8 comprises the same features, elements and/or functions as the headrests 10 described with reference to the previous figures.

Similar to the headrest 10 of FIG. 7, also the headrest 10 depicted in FIG. 8 comprises a supporting structure 16 with a frame element 16a that at least partly surrounds the elastic panel 20 on three sides. The frame element 16a may be manufactured as a single part or as multiple parts. For instance, the frame element 16a may comprise three rails connected to each other, thereby forming the frame element 16a.

In contrast to the embodiment depicted in FIG. 7, the frame element 16a of the headrest 10 shown in FIG. 8 is U-shaped. Therein, the side 29 at the second end 36 of the elastic panel 20 is not attached to the frame element 16*a*. Alternatively, also this side 29 of the elastic panel 20 can be attached to the frame element 16*a*.

Figures 9A, 9B:
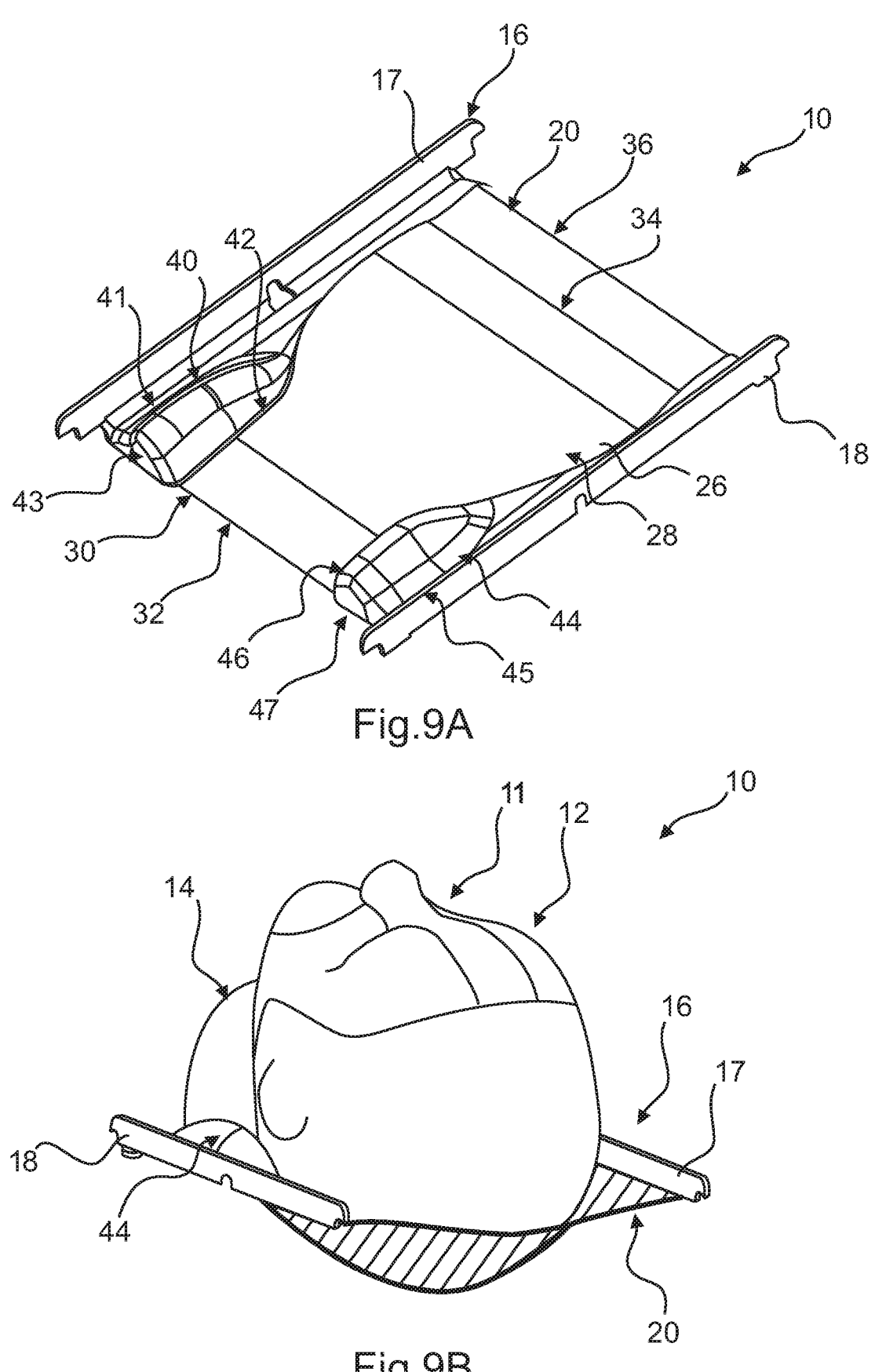
FIGS. 9A to 9C each show a perspective view of a headrest according to another exemplary embodiment of the invention.
Figure 9C:
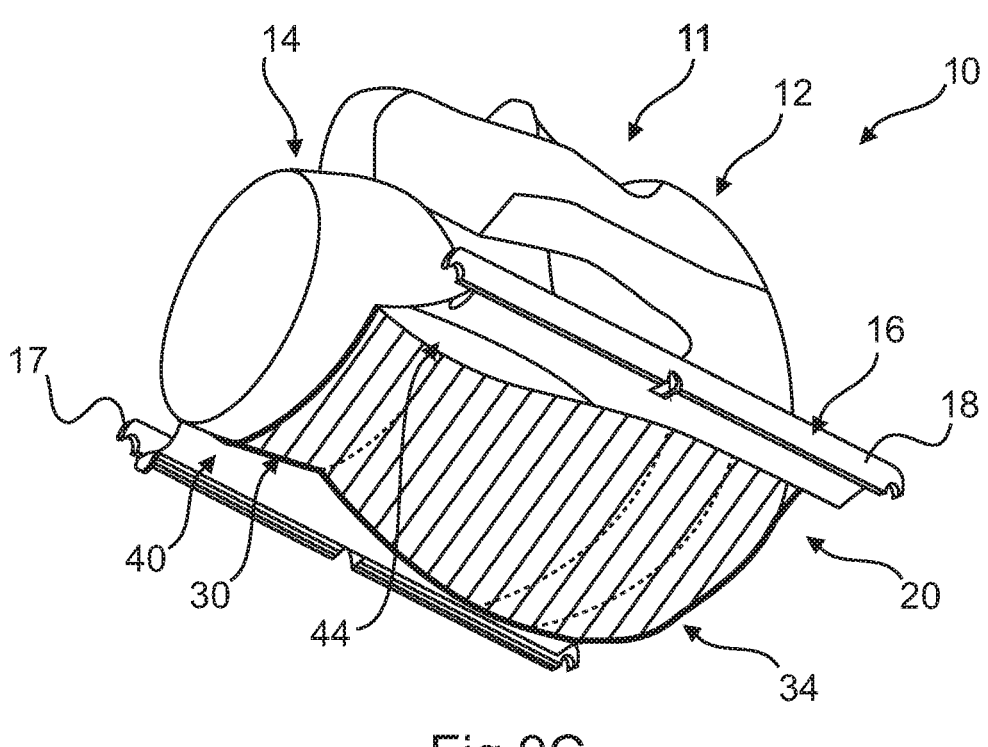

FIGS. 9A to 9C each show a perspective view of a headrest 10 according to another exemplary embodiment of the invention. If not stated otherwise, the headrest 10 of FIGS. 9A to 9C comprises the same features, elements and/or functions as the headrests 10 described with reference to the previous figures.

In the embodiment depicted in FIGS. 9A to 9C the first shaping support 40 and the second shaping support 44 are three-dimensionally and/or anatomically shaped. Specifically, each of the shaping supports 40, 44 is formed in correspondence with an anatomy of the patient 11, particularly an anatomy between the neck 14 and the ears of the patient 11. Therein, in or proximate the first reinforced region 30 of the elastic panel, i.e. the neck support portion 30 of the elastic panel 20, a thickness of the first shaping support 40 gradually or constantly increases along the transverse axis 27 from the first end 41 that is attached to the supporting structure 16 to a center part 43 of the first shaping support 40, and then the thickness of the first shaping support 40 gradually or constantly decreases to the second end 42 of the first shaping support 40. Similarly, in or proximate the first reinforced region 30 of the elastic panel, i.e. the neck support portion 30 of the elastic panel 20, a thickness of the second shaping support 44 gradually or constantly increases along the transverse axis 27 from the first end 45 that is attached to the supporting structure 16 to a center part 47 of the second shaping support 44, and then the thickness of the second shaping support 44 gradually or constantly decreases to the second end 46 of the second shaping support 44.

Moreover, each of the first and second shaping supports 40, 44 extends over the entire length 21 of the elastic panel 20, wherein a width of each of the shaping supports 40, 44 measured along the transverse axis 27 varies along the longitudinal axis 23. Specifically, each of the shaping supports 40, 44 has its largest width proximate or close to the first end 32 of the elastic panel 20, e.g. in or adjacent to the first reinforced region 30 of the elastic panel 20. The width of each of the shaping supports 40, 44 then gradually or constantly decreases along the longitudinal axis 23 from the first end 32 of the elastic panel 20 towards the second reinforced region 34 or the second end 36 of the elastic panel 20. Near or close to the second reinforced region 34, the width of each of the shaping supports 40, 44 then again gradually or constantly increases towards the second end 36 of the elastic panel 20. Accordingly, each of the shaping supports 40, 44 may have the smallest width with respect to other parts of the shaping supports 40, 44, respectively, near or in the middle region 28 of the elastic panel 20, such that each of the shaping supports 40, 44 is concavely formed near or in the middle region 28. This design of the headrest 10 may ensure that the elastic panel 20 encloses as much of the surface of the patient 11 as possible.

In the embodiment depicted in FIGS. 9A to 9C, the elastic panel is attached to the second ends 42, 46 of the shaping supports 40, 44, respectively.

The shaping supports 40, 44 may be integrally formed with the supporting structure 16 or they may be attached and/or detachably attached to the supporting structure 16. The latter may allow to use different shaping supports 40, 44 for different patients 11.

Figure 10:
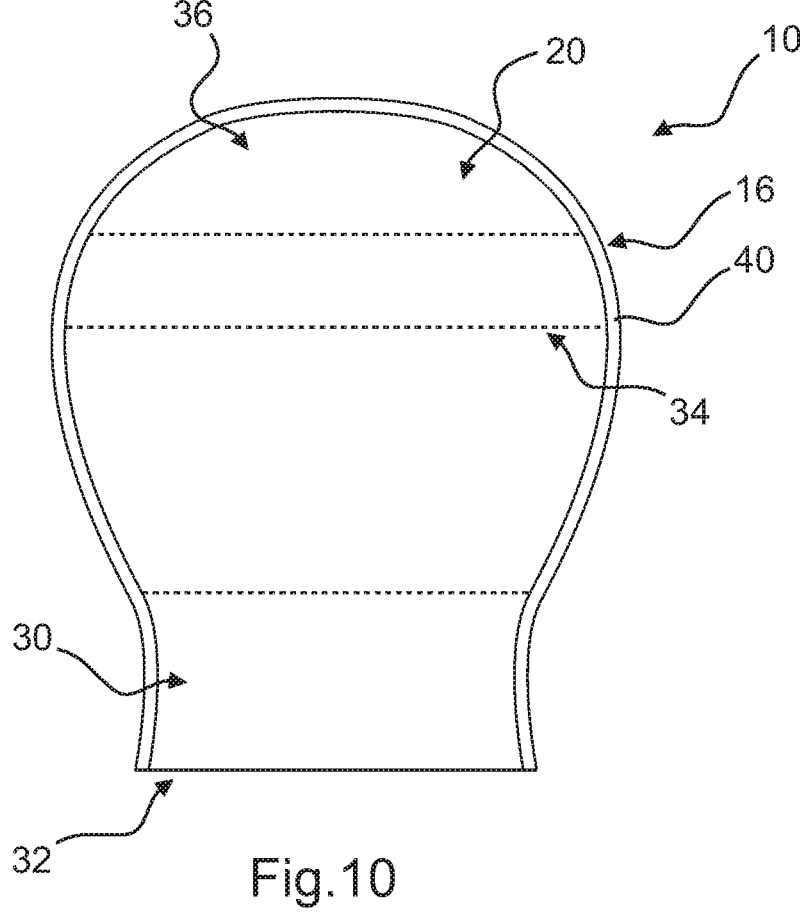
FIG. 10 shows a top view of a headrest according to another exemplary embodiment of the invention.

FIG. 10 shows a top view of a headrest 10 according to another exemplary embodiment of the invention. If not stated otherwise, the headrest 10 of FIG. 10 comprises the same features, elements and/or functions as the headrests 10 described with reference to the previous figures.

In the embodiment depicted in FIG. 10, the headrest 10 comprises a single shaping support 40 which substantially surrounds the patient's head 12 and neck 14 in a plane intersecting the patient's ears along a circumference or perimeter of the patient's head 12 and 14. Therein, the shaping support 40 may substantially have a head- and/or neck-like shape or contour.

Accordingly, in this embodiment, the shaping support 40 may be formed by the supporting structure 16. Alternatively, the shaping support 40 may be attached to at least a part of the supporting structure 16 to allow coupling of the headrest 10 to other parts or components of an immobilization system (not shown).

Figure 11:
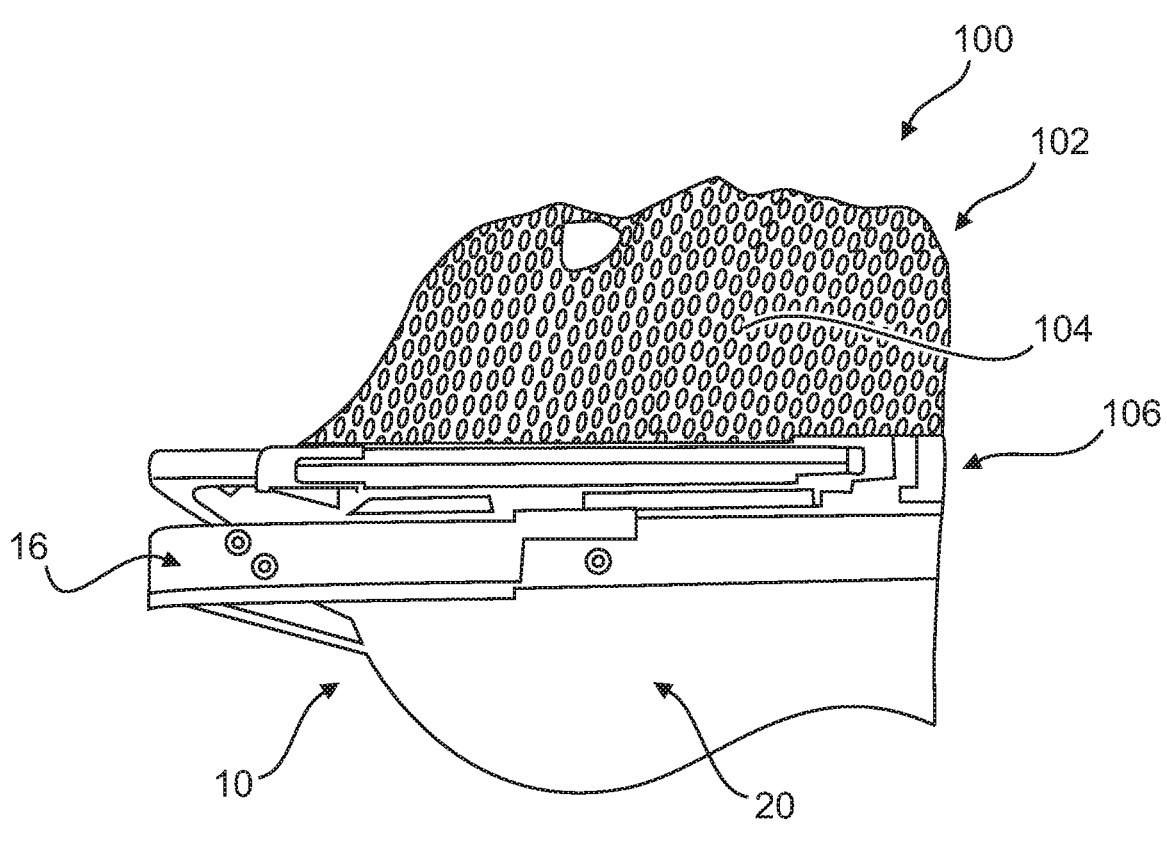
FIG. 11 shows a side view of an immobilization system according to an exemplary embodiment of the invention.

FIG. 11 shows a side view of an immobilization system 100 according to an exemplary embodiment of the invention.

The immobilization system 100 comprises a headrest 10. The headrest 10 can comprise the same features, elements and/or functions as the headrests 10 described with reference to any of the previous figures.

The immobilization system 100 further comprises an immobilization mask 102 coupled to the headrest 10. The headrest 10 and the immobilization mask 102 together form a compartment 106 configured to receive and/or enclose at least a part of the head 12 and/or neck 14 of the patient 11.

The immobilization mask 102 comprises a perforated thermoplastic upper mask sheet 104 or layer 104 of a low temperature thermoplastic material, which previously has been individually adapted to the head 12 in a heated condition thereof so that, after the mask 102 has cooled down and cured, the mask 102 tightly fits to the head 12 to be immobilized.

Figure 12:
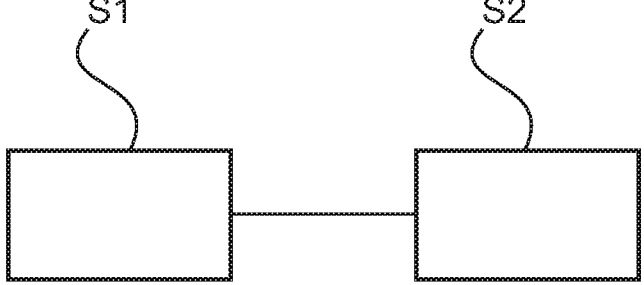
FIG. 12 shows a flowchart illustrating steps of a method for immobilizing a patient according to an exemplary embodiment of invention.

FIG. 12 shows a flowchart illustrating steps of a method for immobilizing a patient 11 according to an exemplary embodiment of invention.

In a first step S1 a headrest 10 is provided. The headrest 10 may refer to a headrest 10 as described with reference to any of the previous figures.

In a second step S2 at least a part of the head 12 and/or at least a part of the neck 14 of the patient 11 is arranged on the elastic panel 20 of the headrest 10, such that at least a part of the elastic panel 20 is stretched and abuts and/or encloses at least a part of the head 12 and/or neck 14 of the patient 11, thereby at least partly immobilizing the head 12 and/or neck 14 of the patient 11.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A headrest for an immobilization system for immobilizing at least a part of a patient, the headrest comprising:
   a. a supporting structure;
   b. a sheet-shaped elastic panel attached to the supporting structure on at least two opposite sides of the elastic panel, wherein the elastic panel comprises a middle region and at least one reinforced region; and
   c. at least one shaping support coupled with the supporting structure and configured to resist downward stretching of the elastic panel in the direction of force exerted by the patient, wherein an end of the at least one shaping support extends away from the supporting structure towards a centre portion of the headrest in a lateral direction and towards the middle region of the elastic panel, d. wherein the supporting structure comprises a first rail arranged on a first side of the elastic panel and a second rail arranged on a second side of the elastic panel opposite to the first side, such that the first and second rails are laterally spaced from one another and the elastic panel is at least partly arranged between the first rail and the second rail, e. wherein the elastic panel is configured to support at least one of a part of a head and/or a part of a neck of the patient, f. wherein at least a part of the elastic panel is stretchable and configured to stretch when at least one of part of the head and/or part of the neck of the patient is arranged on the elastic panel, such that the elastic panel elongates and such that at least part of the elastic panel forms a shape corresponding to a shape of at least one of part of the head and/or part of the neck of the patient, g. wherein the middle region is more stretchable than the at least one reinforced region.

2. The headrest according to claim 1, wherein said at least part of the elastic panel is at least one of reversibly deformable or reversibly stretchable at room temperature.

3. The headrest according to claim 1, wherein the elastic panel comprises one or more elastic sheets for supporting any one or both of (i) and (ii), wherein:

(i) is at least a part of the head, and (ii) is at least a part of the neck of the patient.

4. The headrest according to claim 1, wherein at least one of:

a. a material thickness of the elastic panel in the middle region is smaller than a material thickness of the elastic panel in the at least one reinforced region, or b. the elastic panel comprises a first material in the middle region and a second material in the at least one reinforced region, the first material being different than the second material, such that the middle region is more stretchable than the at least one reinforced region.

5. The headrest according to claim 1, wherein the elastic panel comprises:

a. an elastic sheet arranged in the middle region and in the at least one reinforced region of the elastic panel; and b. at least one further elastic sheet arranged only in the at least one reinforced region of the elastic panel.

6. The headrest according to claim 1, wherein the elastic panel comprises at least one stiffening rib arranged in the at least one reinforced region.

7. The headrest according to claim 1, wherein the elastic panel comprises a first reinforced region on a first end of the elastic panel and a second reinforced region arranged on a second end of the elastic panel opposite to the first end of the elastic panel, and wherein the middle region is arranged between the first reinforced region and the second reinforced region along a longitudinal axis of the headrest.

8. The headrest according to claim 1, wherein at least one of:

a. a contour of at least a part of the end of the at least one shaping support is curvedly formed, or b. a contour of at least a part of the end of the at least one shaping support is formed corresponding to a contour of at least one of said at least a part of the head or at least a part of the neck of the patient.

9. The headrest according to claim 1, wherein at least one of:

a. at least a part of the elastic panel is attached to the at least one shaping support, or b. at least a part of the elastic panel is arranged on top of the at least one shaping support.

10. The headrest according to claim 1, wherein the headrest comprises a first shaping support arranged on a first side of the elastic panel and a second shaping support arranged on a second side of the elastic panel opposite to the first side of the elastic panel, wherein a gap is defined between the ends of the first and second shaping supports for the patient.

11. The headrest according to claim 1, wherein the at least one shaping support is formed integral with the supporting structure.

12. The headrest according to claim 1, wherein the at least one shaping support is detachably coupled to the supporting structure.

13. An immobilization system for positioning or fixing at least a part of a patient, the immobilization system comprising:

a. a headrest for supporting at least one of at least a part of a head or at least a part of a neck of the patient, the headrest including:

(i) a supporting structure;

(ii) a sheet-shaped elastic panel attached to the supporting structure on at least two opposite sides of the elastic panel; and (iii) at least one shaping support coupled with the supporting structure and configured to resist downward stretching of the elastic panel in the direction of force exerted by the patient, wherein an end of the at least one shaping support extends away from the supporting structure towards a centre portion of the headrest, (iv) wherein the supporting structure comprises a first rail arranged on a first side of the elastic panel and a second rail arranged on a second side of the elastic panel opposite to the first side, such that the elastic panel is at least partly arranged between the first rail and the second rail, (v) wherein the elastic panel is configured to support at least one of at least a part of the head or at least a part of the neck of the patient, (vi) wherein at least a part of the elastic panel is stretchable and configured to stretch when at least one of said at least part of the head and neck of the patient is arranged on the elastic panel, such that the elastic panel elongates and such that at least part of the elastic panel forms a shape corresponding to a shape of at least one of said at least part of the head or neck of the patient, (vii) wherein the elastic panel comprises a middle region and at least one reinforced region, the middle region being more stretchable than the at least one reinforced region; and b. an immobilization mask coupled to the headrest, c. wherein the headrest and the immobilization mask together form a compartment configured to receive at least one of at least a part of the head or at least a part of the neck of the patient.

14. The immobilization system according to claim 13, wherein the at least one shaping support is formed integral with the supporting structure or is detachably coupled to the supporting structure.

15. The immobilization system according to claim 13, comprising any one or both of (i) and (ii), wherein:

(i) is a material thickness of the elastic panel in the middle region is smaller than a material thickness of the elastic panel in the at least one reinforced region, and (ii) is the elastic panel comprises a first material in the middle region and a second material in the at least one reinforced region, the first material being different than the second material such that the middle region is more stretchable than the at least one reinforced region.

16. The immobilization system according to claim 13, wherein the elastic panel comprises:

a. an elastic sheet arranged in the middle region and in the at least one reinforced region of the elastic panel; and b. at least one further elastic sheet arranged only in the at least one reinforced region of the elastic panel.

17. The immobilization system according to claim 13, wherein the elastic panel comprises at least one stiffening rib arranged in the at least one reinforced region, and wherein the elastic panel comprises one or more elastic sheets for supporting any one or both of (i) and (ii), wherein:

(i) is at least a part of the head, and (ii) is at least a part of the neck of the patient.

18. The immobilization system according to claim 13, wherein the elastic panel comprises a first reinforced region on a first end of the elastic panel and a second reinforced region arranged on a second end of the elastic panel opposite to the first end of the elastic panel, and wherein the middle region is arranged between the first reinforced region and the second reinforced region along a longitudinal axis of the headrest.

19. The immobilization system according to claim 13, comprising any one or both of (i) and (ii), wherein:

(i) is at least one of at least a part of the elastic panel is attached to the at least one shaping support or at least a part of the elastic panel is arranged on top of the at least one shaping support, and (ii) is at least one of a contour of at least a part of the end of the at least one shaping support is curvedly formed or a contour of at least a part of the end of the at least one shaping support is formed corresponding to a contour of at least one of said at least a part of the head or at least a part of the neck of the patient.

20. The immobilization system according to claim 13, wherein the headrest includes a first shaping support arranged on a first side of the elastic panel and a second shaping support arranged on a second side of the elastic panel opposite to the first side of the elastic panel.

21. A method of immobilizing at least one of at least a part of a head or at least a part of a neck of a patient, the method comprising:

a. providing a headrest including a supporting structure, a sheet-shaped elastic panel attached to the supporting structure on at least two opposite sides of the elastic panel, the elastic panel having a middle region and at least one reinforced region, and at least one shaping support coupled with the supporting structure and configured to resist downward stretching of the elastic panel in the direction of force exerted by the patient, wherein an end of the at least one shaping support extends away from the supporting structure in a lateral direction-towards a centre portion of the headrest and towards the middle region of the elastic panel, wherein the supporting structure comprises a first rail arranged on a first side of the elastic panel and a second rail arranged on a second side of the elastic panel opposite to the first side, such that the first and second rails are laterally spaced from one another and the elastic panel is at least partly arranged between the first rail and the second rail; and b. arranging at least one of a part of the head and/or a part of the neck of the patient on the elastic panel of the headrest, such that at least a part of the elastic panel is stretched, such that the elastic panel elongates and such that at least part of the elastic panel forms a shape corresponding to a shape of at least one of part of the head and/or part of the neck of the patient and encloses at least one of part of the head and/or part of the neck of the patient, thereby at least partly immobilizing at least one of the head and/or the neck of the patient, wherein the middle region is more stretchable than the at least one reinforced region.

* * * * *